United States Patent [19]
Johnson et al.

[11] Patent Number: 5,238,958
[45] Date of Patent: Aug. 24, 1993

[54] SUBSTITUTED α-AMINO ACIDS HAVING SELECTED ACIDIC MOIETIES FOR USE AS EXCITATORY AMINO ACID ANTAGONISTS IN PHARMACEUTICALS

[75] Inventors: Graham Johnson, Ann Arbor; Thomas C. Malone, Canton; Perry M. Novak, Ann Arbor, all of Mich.

[73] Assignee: Warner-Lambert Company, Morris Plains, N.J.

[21] Appl. No.: 512,689

[22] Filed: Apr. 23, 1990

Related U.S. Application Data

[63] Continuation-in-part of Ser. No. 485,348, Feb. 26, 1990, abandoned.

[51] Int. Cl.$^5$ .................... A01N 37/10; C07C 229/00
[52] U.S. Cl. .................... 514/533; 514/538; 514/539; 514/540; 562/426; 562/432; 562/441; 562/442; 562/444; 562/445; 562/449
[58] Field of Search ............ 562/445, 444, 442, 426, 562/431, 432, 441, 449, 451; 514/533, 538, 539, 540

[56] References Cited

U.S. PATENT DOCUMENTS

| | | | |
|---|---|---|---|
| 2,500,019 | 3/1950 | Bergworth | 562/445 |
| 4,065,572 | 12/1977 | Atkinson et al. | 548/306 |
| 4,657,899 | 4/1987 | Rzeszotarski et al. | 514/120 |
| 4,740,615 | 4/1988 | McManus et al. | 562/445 |
| 4,746,653 | 5/1988 | Hutchinson et al. | 514/89 |
| 4,761,405 | 8/1988 | Rzeszotarski et al. | 514/114 |

FOREIGN PATENT DOCUMENTS

| | | |
|---|---|---|
| 8145587 | 11/1987 | Australia . |
| 748446 | 12/1966 | Canada . |
| 0159889 | 10/1985 | European Pat. Off. . |
| 0203891 | 12/1986 | European Pat. Off. . |
| 0233154 | 8/1987 | European Pat. Off. . |
| 0313002 | 4/1989 | European Pat. Off. . |
| 0318935 | 6/1989 | European Pat. Off. . |
| 0330353 | 8/1989 | European Pat. Off. . |
| 917435 | 7/1963 | United Kingdom . |
| 1371896 | 10/1974 | United Kingdom . |
| 2104078A | 3/1983 | United Kingdom . |
| 2156818A | 10/1985 | United Kingdom . |
| 2198134 | 6/1988 | United Kingdom . |

OTHER PUBLICATIONS

Scrip #1067 Jan. 13, 1986 (p. 22).
Neurology and Neurobiology, vol. 24 (19–26 "Excitatory Amino Acid Transmission" J. C. Watkins, et al 1987.
Tetrahedron 33:2715–7 (1977) D. Ben–Ishai, et al "The Synthesis of p–Substituted D,L-Phenylglycines by the Amidoalkylation of Benzylchloride and N-Benzyl-benzamide".

*Primary Examiner*—Alan L. Rotman
*Assistant Examiner*—Raymond Covington
*Attorney, Agent, or Firm*—Joan Thierstein; Ronald A. Daignault

[57] ABSTRACT

The present invention is novel substituted α-amino acids, pharmaceutical compositions, methods of use, and preparations therefore having utility for treating disorders which benefit from blockade of aspartate and glutamate receptors.

22 Claims, No Drawings

SUBSTITUTED α-AMINO ACIDS HAVING SELECTED ACIDIC MOIETIES FOR USE AS EXCITATORY AMINO ACID ANTAGONISTS IN PHARMACEUTICALS

This application is a continuation-in-part of U.S. application Ser. No. 07/485,348 filed Feb. 26, 1990, now abandoned.

BACKGROUND OF THE INVENTION

Among excitatory amino acid receptor antagonists recognized for usefulness in the treatment of disorders are those that block N-methyl-D-aspartate (NMDA) receptors.

For example, heterocycles containing nitrogen, and having phosphonic acid and carboxylate substituents, are found in European Application Publication Numbers 0159889 and 0203891 and Australian Application Number 81455/87 which disclose utility for the treatment of nervous system disorders. The disorders disclosed which are responsive to blockade of the NMDA receptor include cerebral ischemia, muscular spasms (spasticity), convulsive disorders (epilepsy), and anxiety. These compounds, however, are readily distinguished from the compounds of the present invention both by the nitrogen containing heterocycles and by the various substituents thereon.

Aliphatic α-amino acids are disclosed in British Patent Numbers 2,104,078 and 2,156,818. The first of these, Number 2,104,078, includes 2-amino-7-phosphonoheptanoic acid (APH) disclosed for use in treating Huntington's disease, Alzheimer's disease, and certain forms of epilepsy as well as for use in the prevention of brain damage associated with stroke (see SCRIP #1067, Jan. 13, 1986, page 22). The second of these, 2,156,818, discloses usefulness for treating epilepsy, disorders associated with excess growth hormone (GH) or luteinizing hormone (LH) secretion, schizophrenia, depression, CNS degenerative disorders, and cerebral hypoxic conditions.

More particularly, U.S Pat. No. 4,657,899 discloses compounds of the formula

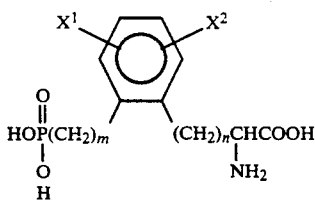

wherein n and m=0, 1, 2, or 3 and $X^1$ and $X^2$ are the same or different and are selected from the group consisting of hydrogen, lower alkyl, halogen, —CH=CH—CH=CH—, amino, nitro, trifluoromethyl, or cyano, having activity as anticonvulsants, analgesics, and cognition enhancers through the antagonism of specific excitatory amino acid neurotransmitter receptors.

U.S. Pat. No. 4,761,405 teaches a cycloalkyl ring system having substituents similar to U.S Pat. No. 4,657,899.

Additionally, α-amino acids on a carboxy-containing phenyl ring are disclosed in U.S. Pat. No. 4,065,572; British Patent Numbers 1,371,896 and 917,435 and Canadian Patent Number 748,446. However, these disclosures have different substituents.

The novel substituted α-amino acids of the present invention are not made obvious by these disclosures. In fact, clearly the disclosure of U.S. Pat. No. 4,657,899 is limited to a specific ortho positioning of phosphonic acid and amino acid residues on a phenyl ring. Such a limitation teaches away from the novel compounds of the present invention.

An understanding of the role of excitatory amino acids is expanded by J. C. Watkins, et al, in "Recent Advances in the Pharmacology of Excitatory Amino Acids", *Excitatory Amino Acid Transmission: Neurology and Neurobiology*, 24:19-26, Ed by Hicks, Lodge and McLennan, Publisher: Alan R Liss, Inc , New York, 1987.

An additional reference is now found to compounds, for example, for the treatment of diseases responding to a blockade of NMDA-sensitive receptors, in European Application Publication Number 0233154, of the formula

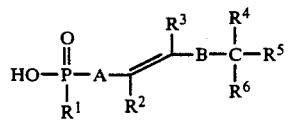

showing a basic difference in that the phosphorus containing substituent and the amino/carboxy containing substituent are linked through a straight chain double bonded C=C linkage and not as substituents on a common aryl ring.

Then, on the other hand antagonists to the NMDA sensitive excitatory amino acid receptors are shown in U.S. Pat. No. 4,746,653, filed Feb. 28, 1986, to include substituted saturated pyridinyl ring systems common to both a phosphorus containing and carboxy or carboxy derivatized substituent.

More recently, the British Patent Application Number 2,198,134, filed Oct. 30, 1986, but not published before Jun. 8, 1988, teaches compounds useful for treating epilepsy including anticonvulsant activity shown from inhibition of NMDA in excitatory amino acid systems having the formula

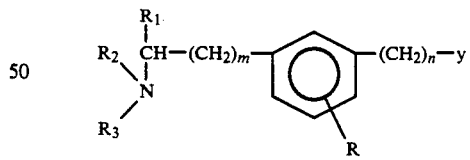

wherein $R_1$ is a carboxy or carboxy containing analogue and y is a

containing substiluent. However, the present invention is defined by a scope not taught within the broad disclosure of this application and, therefore, represents an advance not made obvious therein.

Although a related reference teaches "The Synthesis of p-Substituted D,L-Phenylglycines by the Amidoalkylation of Benzylchloride and N-Benzylbenzamide", *Tetrahedron* 33:2715-7 (1977) by D. Ben-Ishai, et al, it does not make obvious the use of the process for phosphonate containing derivatives.

Also known is the use of a 4-tetrazolylmethyl group on a piperidinyl-2-carboxylic acid moiety for use as an excitatory amino acid receptor antagonist as shown by a poster by Dr. P. L. Ornstein, et al, at the "First Princeton Drug Research Symposium" on May 21st to 23rd, 1989 and as disclosed in European Patent Application Number 330,353. However, no teaching is disclosed for the present from the piperidine of Ornstein's poster.

Finally, EP Publication Number 318935, a copending application, and European Patent Application Publication Number 313002 both disclose the use of a phosphonyl acid group.

Not all piperidinyl, pyridinyl or other heterocyclic ring systems are included in this Background as it is deemed such systems are different from the present invention compounds.

SUMMARY OF THE INVENTION

The present invention is a novel compound selected from the formula (IA, IB or IC)

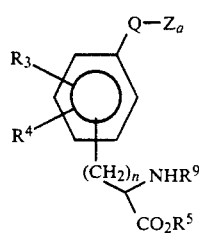   IA or

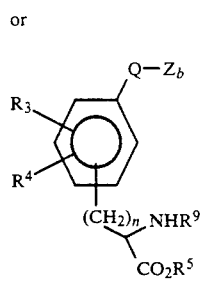   IB or

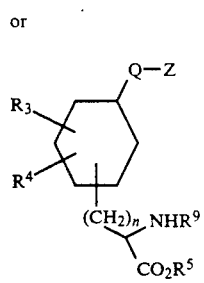   IC or a pharmaceutically acceptable acid addition or base salt thereof; wherein the group ($I_a$)

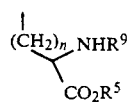   $I_a$ is ortho, meta or para to the group ($I_b$, $I_c$ or $I_d$)

   $I_b$

   $I_c$ or

   $I_d$ wherein
(1) n is 0, 1, or 2;
(2) $R^5$ is independently hydrogen or a pharmaceutically acceptable labile ester residue;
(3) $R^3$ and $R^4$ are independently hydrogen, hydroxy, lower alkyl, aryl, arylalkyl, lower alkoxy, lower alkylthio, halogen, trifluoromethyl, lower alkoxy-methyl, or taken together with adjacent ring carbons are —CH=CH—CH=CH—;
(4) $R^9$ is hydrogen or a protecting group;
(5) Q is —$(CH_2)_m$—, —(CH=CH)—, —$CH_2$—(CH=CH)—, or (CH=CH)—$CH_2$— wherein m is 0, 1, 2, or 3 with the proviso that in the formula IA m cannot be 0 when Z is $CO_2R^{20}$ and both $R^3$ and $R^4$ are hydrogen, and also in the formula IA the m cannot be 0 when Z is $CO_2R^{20}$ and $R^3$ is hydrogen and $R^4$ is alkyl or hydroxy or lower alkoxy or halogen;
(6) $Z_a$ is selected from
  (a) —$PO_2R^{20}R^{21}$ wherein $R^{20}$ and $R^{21}$ are independently selected from hydrogen, lower alkyl, lower alkenyl, aryl, aryl lower alkyl, or a pharmaceutically acceptable labile ester group,
  (b) —$CO_2R^{20}$ wherein $R^{20}$ is as defined above, or (c) 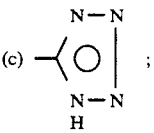 ;

$Z_b$ is $PO_3R^{20}R^{21}$ wherein $R^{20}$ and $R^{21}$ are as defined above; n is 0 or 1 and m is 0, 1, or 2; and $R^3$ or $R^4$ are hydroxy;

Z is $PO_3R^{20}R^{21}$, $PO_2R^{20}R^{21}$, $CO_2R^{20}$ or
wherein $R^{20}$ and $R^{21}$ are as defined above.

Preferably the compounds of formula IA and IB are limited so that when the group $I_a$ is para to the group $I_b$ then n may be 0 is 0, 1, 2, or 3 and n may be 1 when m is 0 or 2; that when the group $I_a$ is meta to the group $I_b$ or $I_c$ then n may be 0 when m is 1 or 2, n may be 1 when m is 0, 1, or 2, and n may be 2 when m is 0; and that when group $I_a$ is ortho to group $I_b$ or $I_c$ then n may be 1, when m is 1, 2, and 3.

More preferred are the compounds IA and IC wherein $Z_a$ and Z are respectively $CO_2R^2$ or

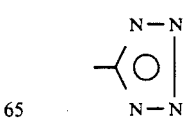

An additional aspect of the present invention is a compound selected from the formula

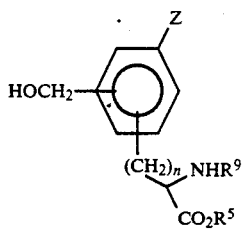

and

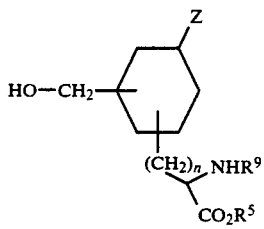

wherein n, Z, $R^5$, and $R^9$ are as defined above and preferred compounds of ID and IE have the group

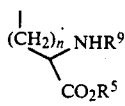

para to Z when n is 0 or 1 or meta to Z when n is 1 or 2.

Again, more preferred of the compounds of ID or IE are those where Z is $CO_2R^2$ or

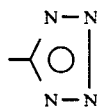

The present invention is also a pharmaceutical composition for the treatment of cerebrovascular disorders in which excitatory amino acid antagonists are useful comprising an amount effective to block glutamate or aspartate (NMDA) receptors of a compound of the formula 1 as defined above and a pharmaceutically acceptable carrier.

Such disorders include cerebral ischemia or cerebral infarction, resulting from a range of conditions, such as thromboembolic or hemorrhagic stroke, cerebral vasospasm, hypoglycemia, cardiac arrest, and status epilepticus, and also include schizophrenia, epilepsy, neurodegenerative disorders, Alzheimer's disease, or Huntington's disease. They are also useful as analgesics Further, cerebrovascular damage may be treated prophylactically or therapeutically where a finite risk of the damage is understood to be present by an ordinarily practicing physician, such as in surgical procedures.

Thus, further the present invention is a method of treating cerebrovascular disorders particularly in which amino acid antagonists are useful in a human suffering therefrom or at risk of such disorders which comprises administering a compound of the formula I as defined above in a unit dosage form.

Finally, the present invention is also novel processes. In the processes a compound of formula IA, IB, and ID are hereinafter referred to as the compound of formula I for convenience.

One of the novel processes is for the preparation of a compound of formula I wherein n is 0 and m is 1, 2, or 3 as defined above which comprises Step (1) reacting a compound of the formula (X)

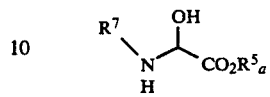

wherein $R^5_a$ is $R^5$ but not including hydrogen and $R^7$ is an acid stable protective group, such as a benzoyl, benzyloxycarbonyl, or ethoxycarbonyl;

with a compound of the formula XI

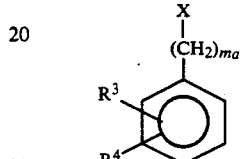

wherein $m_a$ is 1, 2, or 3, X is $CO_2H$, chloro or bromo, and $R^3$ and $R^4$ are as defined above;

in the presence of methanesulfonic acid or strongly dehydrating acids such as concentrated sulfuric acid over a period of forty-eight hours at room temperature to obtain a compound of the formula XII

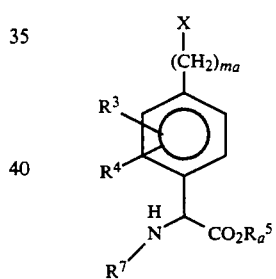

wherein $R^3$, $R^4$, $R^5_a$, and $R^7$ are as defined above when one of $R^3$ and $R^4$ are not H then $R^3$ and $R^4$ may be a group whose regiochemical direction influence is compatible with this reaction. Selection of such groups would be apparent to one of ordinary skill in the art.

Step (2) the compounds of the formula XII are then treated with a compound of the formula (XIII)

$R^8Z^1$       XIII wherein $R^8$ is sodium, potassium, or the like and $Z^1$ is —CN, —$PO_3R^{20}R^{21}$ or —$PO_2R^{20}R^{21}$, wherein $R^{20}$ and $R^{21}$ are as defined above except that where required each may be a protecting group such as when the $R^{20}$ functions as a precursor to a hydrogen;

in a solvent such as tetrahydrofuran, diethyl ether, dimethylformamide, acetonitrile, or the like at temperatures from room temperature to reflux over a period of one to forty-eight hours to obtain the compound of the formula (XIV) (alternatively the phosphinoalkyl derivatives of formula XIV can be obtained by an Arbuzov reaction with phosphinate or an equivalent).

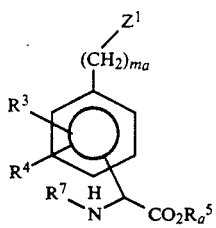

wherein $R^3$, $R^4$, $Z^1$, $R^7$, $R^5_a$, and $m_a$ are as defined above;

The compounds of the formula XIV may be treated to remove protective groups, to protonate the acidic residues or to esterify the acid groups, if desired.

This process is summarized in Scheme A as follows:

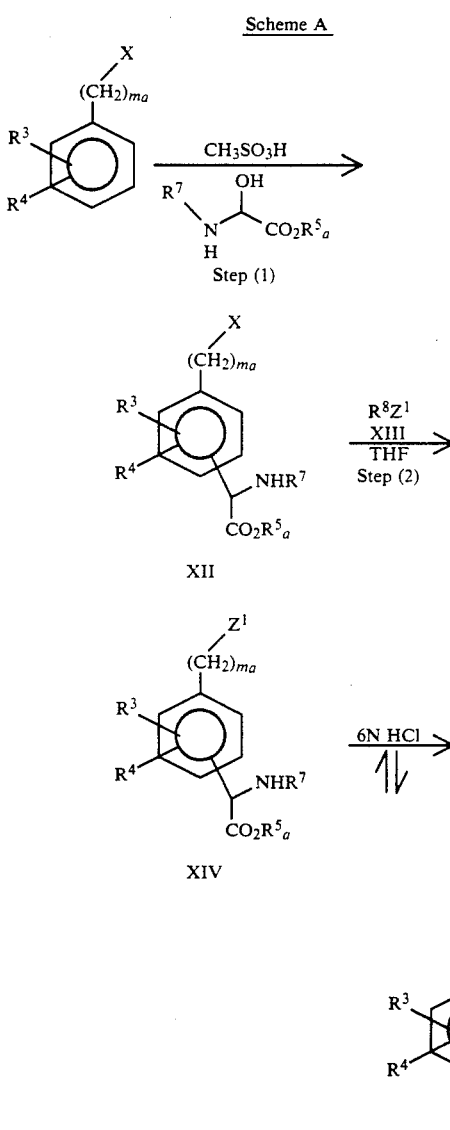

In another process of the present invention analogous to known processes the compounds of the formula I wherein groups $I_a$ and $I_b$ are meta, n is 0, and m is 1 is prepared in a process which comprises Step (1) reaction of a compound of the formula (XX)

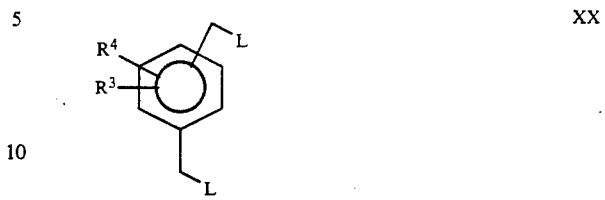

wherein L is a leaving group such as halogen, e.g., I, Br, or Cl or a methanesulfonate, toluenesulfonate, or trifluoroacetate and one L-containing group is meta or para to the other L, and $R^3$ and $R^4$ are as defined above; with a compound of the formula (XXI)

$R^8Z^1$   XXI wherein $R^8$, is as defined above and Z is $-PO_2R^{20}R^{21}$, $PO_3R^{20}R^{21}$ or $-CN$;

in a solvent such as diethyl ether, tetrahydrofuran, dimethylformamide, or dimethoxyethane, and the like to obtain a compound of the formula (XXII)

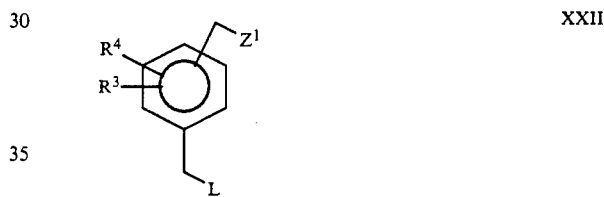

wherein $R^3$, $R^4$, and L are all as defined above;

Step (2) Sodium methoxide in methanol or sodium ethoxide in ethanol or the like is treated with 2-nitropropane and the compound of formula XXII to obtain a compound of the formula (XXIII)

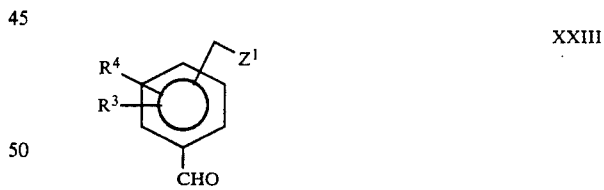

Step (3) the compound of formula (XXIIIa wherein $Z^1$ is CN)

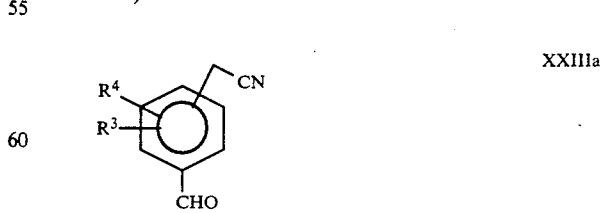

wherein the CHO is protected and is treated either in a manner analogous to the processes of British Patent Number 2,104,078A to obtain a compound of the formula

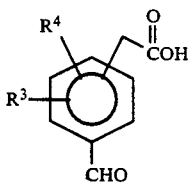 XXIIIb or is treated with NaN₃ and NH₄Cl in a solvent such as N-methylpyrrolidinone (NMP), or dimethylformamide (DMF) at a temperature of from about 150° C. to 200° C. or treated with Bu₃SnN₃ in a manner similar to that described in EP 330,353 or as described in *J. Organometallic Chem.* 33:337-346 (1971) to obtain a compound of the formula

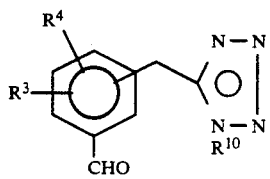 XXIIIc wherein $R^{10}$ is H or $SnBu_3$ (wherein Bu is butyl)

Step (3) the compound of formula XXIII, wherein the CHO is no longer protected wherein Z is $PO_3R^{20}R^{21}$, $PO_2R^{20}R^{21}$, COOH, or tetrazolyl, is then stirred in a solution of sodium metabisulfite in water to which concentrated ammonium hydroxide is then added followed by the addition of NaCN to obtain a compound of the formula (XXIV)

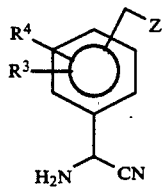 XXIV wherein Z is as defined above;

Step (4) the compound of the formula XXIV may be hydrolyzed, if necessary, to obtain the compound of formula I wherein $R^3$ and $R^4$ is as defined above and $R^5$ is hydrogen and optionally treated further to obtain the formula I wherein $R^{20}$, $R^{21}$, and $R^5$ are a desired ester or amide residue or pharmacologically acceptable base salt thereof.

This process is summarized in Scheme B as follows:

Scheme B

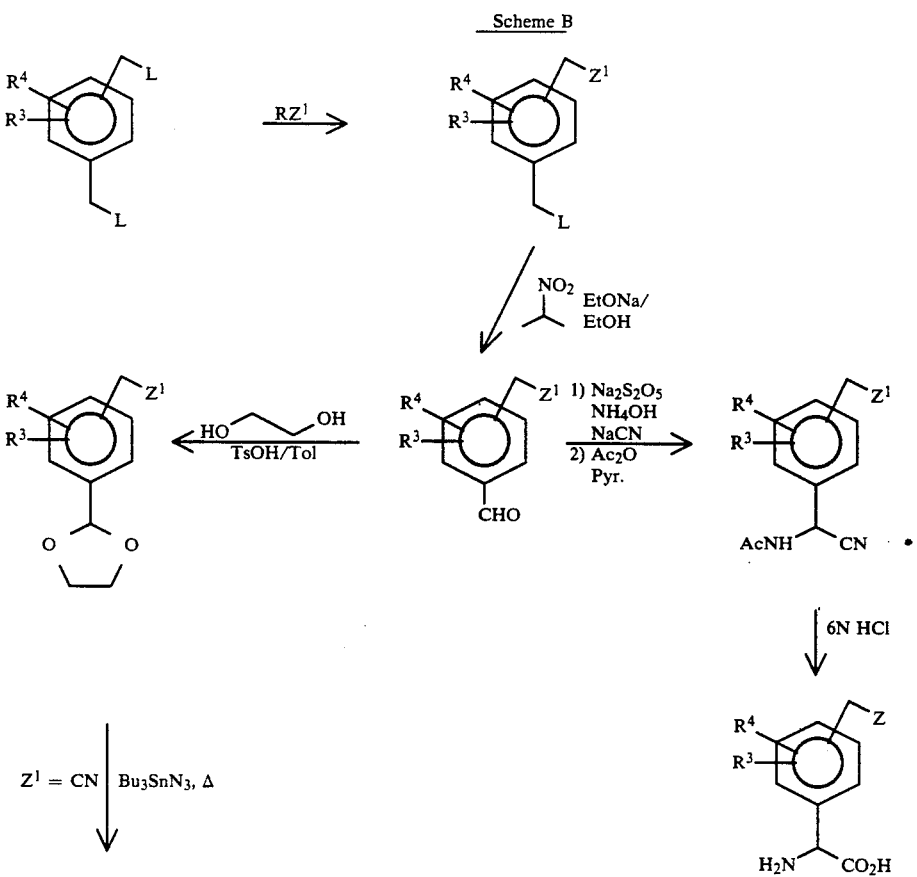

-continued
Scheme B

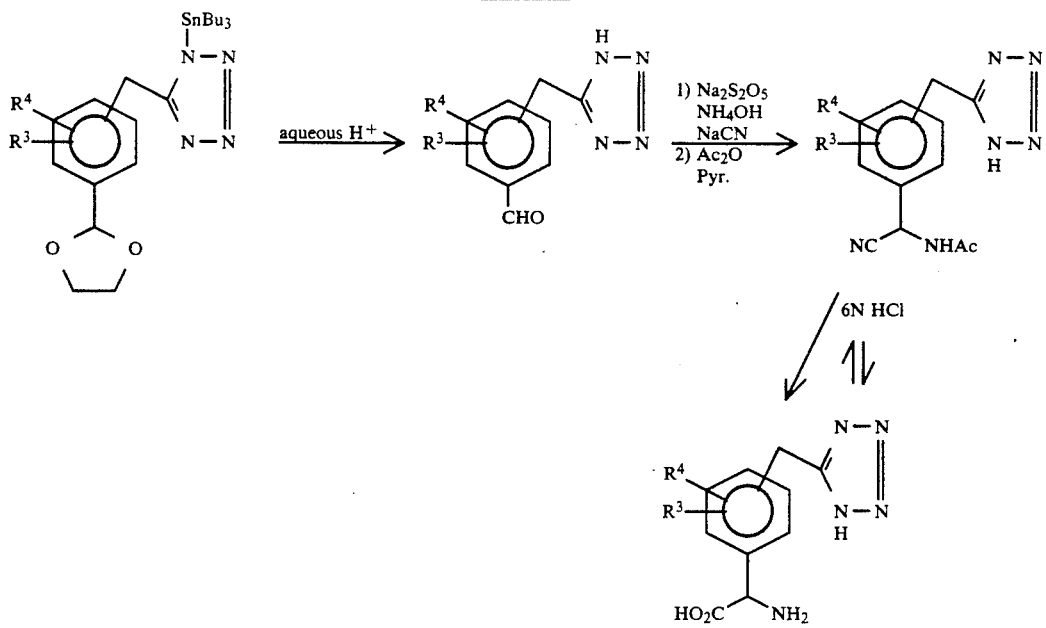

Another process to prepare the compounds of the present invention of formula I wherein one halogen containing group is ortho, meta or para to the other halogen and n is 1 and m is 1 is analogous to that of U.S. Pat. No. 4,657,899 and is shown as follows in Scheme C. Optionally, products of this scheme can also be further reacted to obtain desired salts or labile esters or amides thereof.

Scheme C

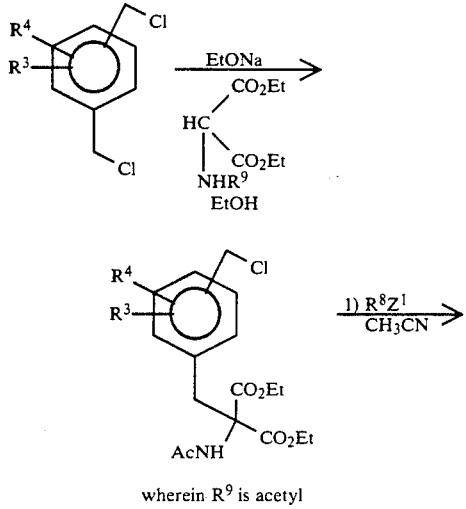

wherein R[9] is acetyl

-continued
Scheme C

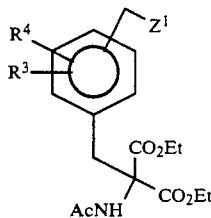

Another process of the present invention is for the preparation of compounds of the formula I wherein groups $I_a$ and $I_b$ are para, meta or ortho; n is 0; and m is 2 which comprises Step (1) treating a compound of the formula (XXX)

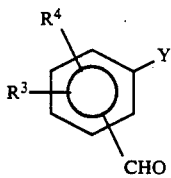

wherein Y is Br, I or $OSO_2CF_3$, $R^3$ and $R^4$ are as defined above;

in a solvent such as ethanol, methanol, and the like with ammonium chloride in water, then a solution of potassium cyanide also in water is added after which the product is treated with HCl in ether to obtain the compound of formula (XXXI)

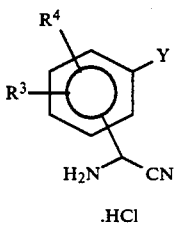

which is treated to add a protecting group to the amino substituent;

Alternatively, the compound of formula XXXI is treated to convert CN to an ester group before treating with a compound of formula XXXII;

Step (2) the protected compound of formula XXXI wherein Y is Br, I or $OSO_2CF_3$ is then treated with a compound of the formula (XXXII)

$H^2C=CHZ^2$   XXXII wherein $Z^2$ is CN, $COOR^{20}$, $PO_3R^{20}R^{21}$, $PO_2R^{20}R^{21}$; or

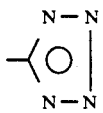

in the presence of palladium acetate, tri-orthotolylphosphine and tri-n-butylamine in a solvent such as xylene, toluene, and the like to obtain the compound of the formula (XXXIII)

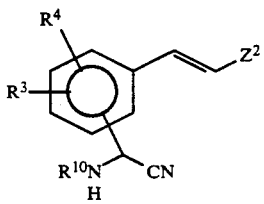

wherein $R^{10}$ is a protecting group an $Z^2$, $R^3$, and $R^4$ are as defined above;

In the instance where $Z^2$ in the compound of formula XXXIII is CN, the compound may be treated with $NaN_3$ and $NH_4Cl$ in DMF or NMP or as illustrated in EP 330,353 or the *J. Organometallic Chem.* 33:337–346 (1971), to obtain the compound of formula (XXXIII$_a$)

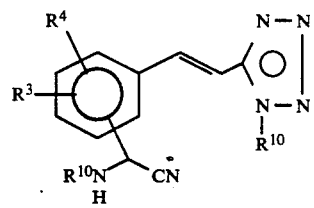

Step (3) then the compound of formula XXXIII or XXXIII$_a$ is optionally hydrogenated and then hydrolyzed or hydrolyzed to obtain the compound of formula 1.

This process is summarized in Scheme D as follows:

Scheme D

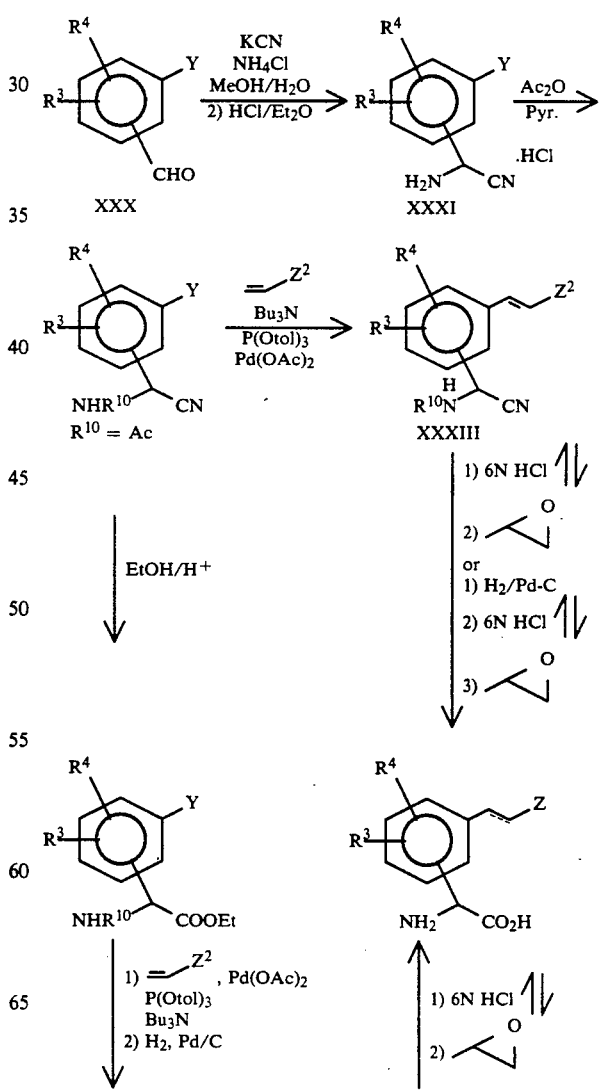

-continued
Scheme D

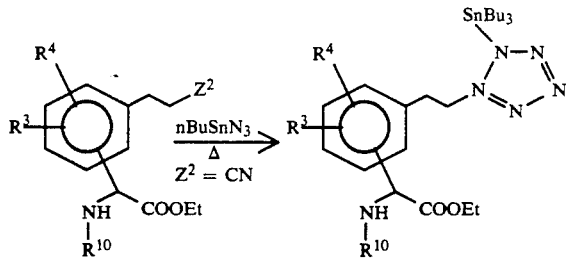

Variations in this sequence of treatment is within the skill of an ordinary artisan.

Another process of the present invention to prepare the compounds of the present invention of the formula I wherein groups $I_a$ and $I_b$ are ortho, meta or para and wherein n is 1 and m is 2 comprises Step (1) treating a compound of the formula XL

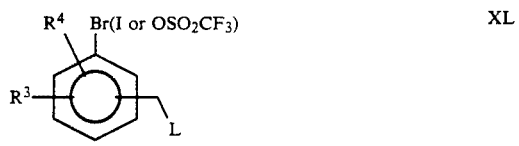

wherein L, $R^3$, and $R^4$ are as defined above with diethylacetamidomalonate, dimethylacetamidomalonate, diethylformamidomalonate, or the like in the presence of sodium ethoxide in ethanol or sodium methoxide in methanol or the like to obtain a compound of the formula XLI.

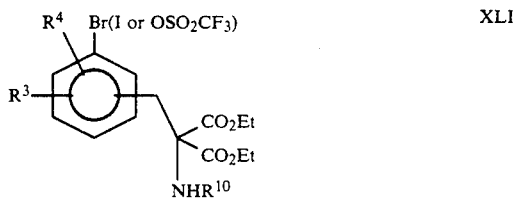

wherein $R^{10}$ is as defined above and Et is ethyl;

Step (2) the compound of formula XLI is treated in a manner analogous to Steps (2) and (3) in Scheme D above to obtain the compound of formula I wherein n is 1 and m is 2;

Additionally, alternative methods can be shown for Step (2) providing various compounds of the invention wherein n is 1 and m is 0 as follows:

Step (2), the product of Step (1), compound of formula XLI, is treated with $HPO_3(C_2H_5)_2$, $HPO_2(C_2H_5)R_{20}$ or CO plus methanol in a palladium catalyzed exchange of the Br, I, $OSO_2CF_3$ substituent using conditions analogous to those found in *Synthesis*, 56-57 (1981).

Step (2) Alternatively, the product of Step (1), compound of the formula XLI, is treated with CuCN in DMF at temperatures between 150° C. to 220° C. or by other methods known to those skilled in the art such as those described in *Chem. Rev.* 87:779-779 (1987) and *J. Chem. Soc. Perkin I* 1365 (1989).

Step (3) Each of the above Step (2) is followed by hydrolysis with optional treatment to obtain a compound of the formula (XLII)

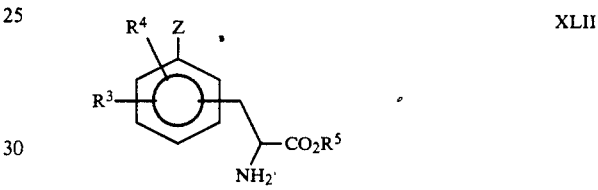

wherein $R^3$, $R^4$, $R^5$, and Z are as defined above.

The substituent Br(I or $OSO_2CF_3$) may also be meant to include equivalents selected by one of ordinary skill in the art including, for example, mercuric halides, and the like. (See Heck, Richard F., *Palladium Reagents in Organic Synthesis*, Academic Press (1985)).

Again, variations to react intermediates having the substituents Br(I or $OSO_2CF_3$) to obtain $CH_2CN$ and then further to obtain $CH_2CO_2H$ or can be accomplished in the same manner as set out above using appropriate analogous reaction conditions.

These various process steps can be shown as follows in Scheme E.

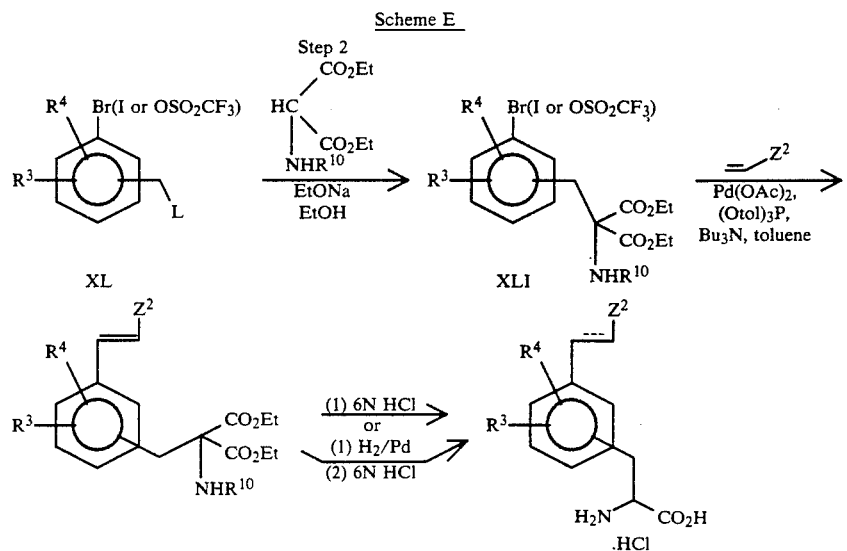

Scheme E

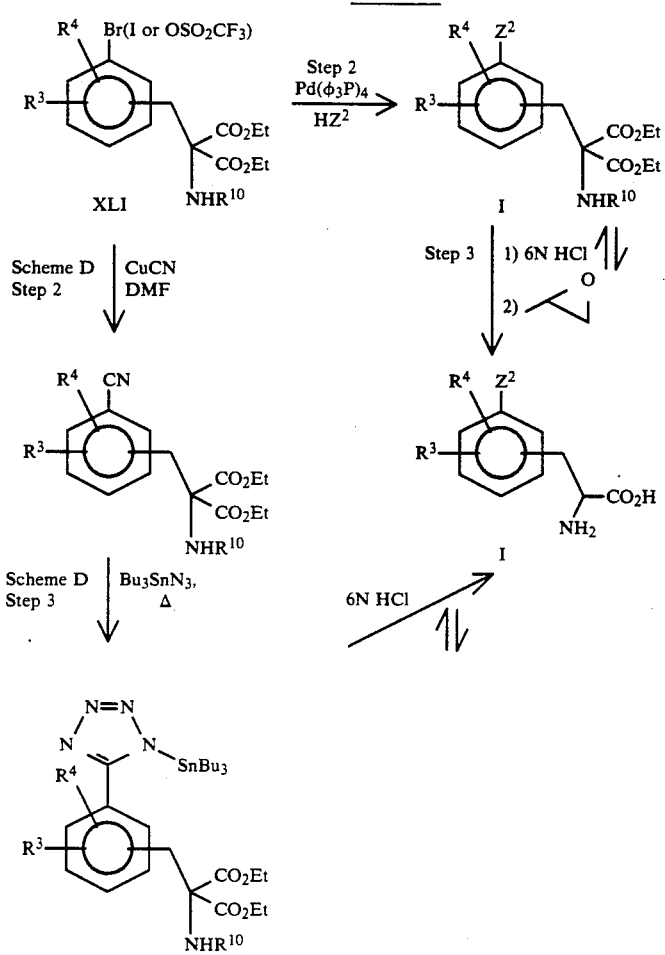

Finally, the present invention is a process for the preparation of a compound of the formula I wherein n is 2 and m is 0, comprising Step (1) treating a compound of the formula (LX)

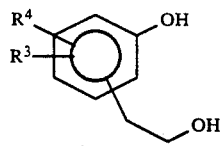

with bistrifluoromethanesulfonyl aniline of the formula

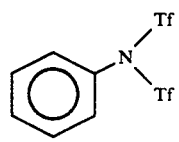

in methanol in the presence of diisopropylethylamine using conditions analogous to those described in *J. Am. Chem. Soc.* 109(9):2381 (1987) to obtain a compound of the formula (LXI)

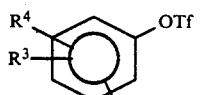

wherein Tf is the triflate residue;

Step (2) the compound of the formula LXI is then treated with a compound of the formula $HZ^2$ wherein $Z^2$ is as defined above in the presence of a palladium catalyst as described in *J. Am. Chem. Soc.* 109(9);2381 (1987) or, alternatively, the triflate provides the substituent which can be converted to $CH_2CN$ and then either $CH_2CO_2H$ or

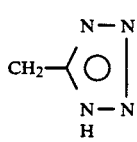

to obtain a compound of the formula (LXII)

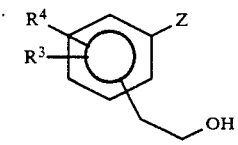

LXII

The compound of formula LXII can be treated in a manner known, or analogous to known processes, to obtain compounds of formula I wherein n is 2 and m is 0, having the desired ester or salt.

Also among the novel processes for the preparation of the compounds of Formula I wherein n is 0 and m is 1 as defined above are the following:

A process for preparing the compound of the Formula I wherein $R^3$ and $R^4$ are hydrogen, Q is —$CH_2$— is and Z is —COOH comprises (1) reacting the compounds of formula

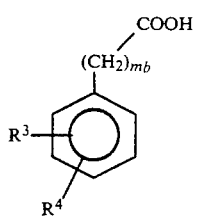

1 with a compound of the formula

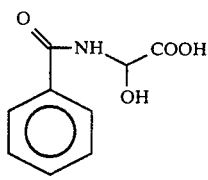

2 in a manner similar to that described in Scheme A, Step 1, obtain the compound having a protected amine group of the formula

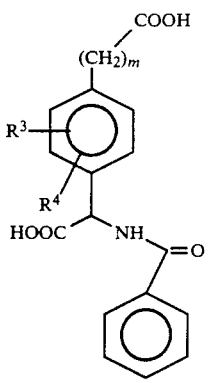

3

For purposes of purification, the compound of formula 3 may be esterified with $CH_2N_2$ at about $-40°$ C. to $+35°$ C. preferably 25° C. for from 5 to 45 minutes, preferably 15 minutes to obtain a compound of the formula

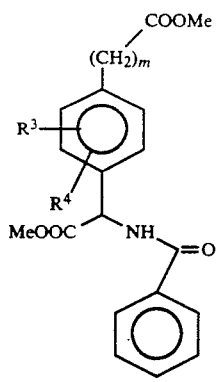

which may then be treated with acid such as 6N HCl at reflux until the desired product of the formula

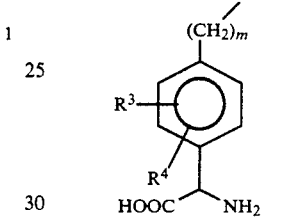

$I_1$ is obtained.

On the other hand a process for preparing a compound of the formula I wherein one of $R^3$ and $R^4$ is hydrogen and the other of $R^3$ and $R^4$ is hydroxy at the position para to the amin acid containing substituent and the COOH group meta to the amine substituent comprises (1) treating a compound of the formula

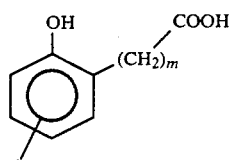

5 with a protected hydrox-vhippuric acid in the presence of formic acid to obtain the compound of the formula

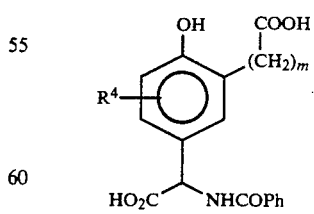

3 wherein Ph is phenyl;

As an optional step to aid purification, the compound of Formula 3 may be treated with an alkanol such as methanol, ethanol or the like in an acid medium to obtain the compound of the formula

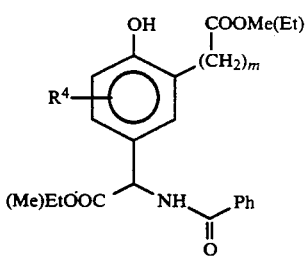

wherein Ph is as defined above, Et is ethyl and Me is methyl; and following purification, then treating with an acid, such as 6N HCl the compound of the Formula 6 (see Scheme F) to obtain the compound free of protecting groups having the formula

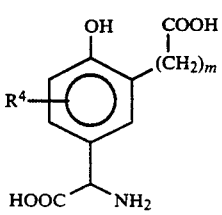

A process for preparing the compound of the formula I wherein one of $R^3$ and $R^4$ is an OH in a position ortho to the group containing the COOH that is para to the amino acid containing group comprised (1) treating a compound of the Formula

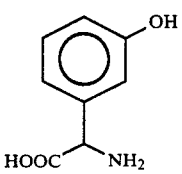

with acetic anhydride to obtain a compound showing an alternative protecting group on the amino substituent of the formula

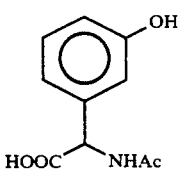

wherein Ac is acetyl (2) treating the compound of the formula 8 with $CH_2N_2$ to esterify the COOH for protecting it yielding a compound of the formula

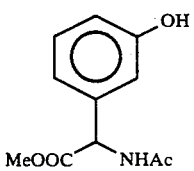

wherein Me is methyl and Ac is acetyl;

(3) treating the compound of the formula 9 with allyl bromide in the presence of $K_2CO_3$ in a solvent such as acetone to obtain the compound of the formula

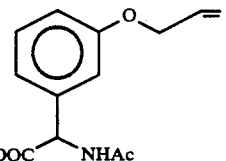

wherein Me is methyl and Ac is acetyl;

(4) reacting the compound of the formula 10 in p-dichlorobenzene at about 350° C. to obtain the compound of the formula

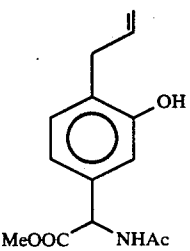

wherein Me is methyl and Ac is acetyl;

(5) treating the compound of the formula 11 with benzoyl chloride in a solvent system such as chloroform and triethylamine or pyridine to obtain the compound

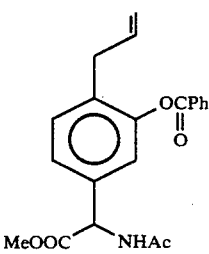

wherein Ph is phenyl, Me is methyl, and Ac is acetyl;

(6) treating the compound of the formula 12 with sodium metaperiodate and $RuCl_3$ in a solvent system such as $H_2O$, $CH_3CN$ or benzonitrile and $CCl_4$ at about +5° C. to +40° C., preferably 25° C. to obtain the compound of the formula

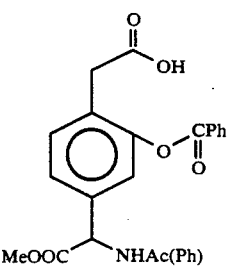

wherein Ph is phenyl, Me is methyl, and Ac is acetyl;

(7) the compound of the formula 13 may be treated by refluxing in acidic medium such as 6N HCl to obtain the compound of the formula

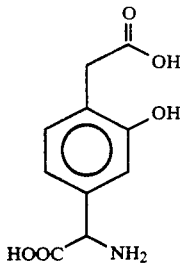

A process for preparing a compound of formula I wherein Q is CH$_2$, Z is tetrazole, and one of R$^3$ and R$^4$ is OH ortho to the tetrazole containing substituent comprises (1) treating a compound of the formula 12 as defined above in a solvent such as dichloromethane with ozone followed by treating with dimethylsulfide to obtain the compound of the formula

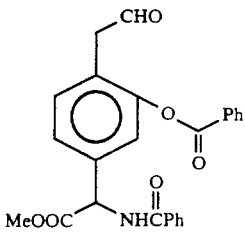

14 wherein Ph is phenyl and Me is methyl;

(2) treating the compound of the formula 14 with O,N-bistrifluoroacetylhydroxylamine in a solvent such as toluene in the presence of pyridine to obtain the compound of the formula

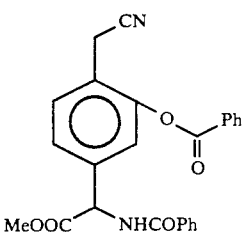

15 wherein Ph is phenyl and Me is methyl;

(3) treating the compound of formula 15 in a solvent such as dioxane with tri-n-butyltinazide to obtain the compound of the formula

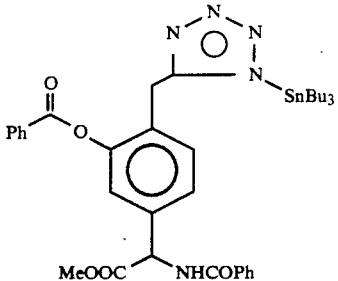

16 wherein Ph is phenyl and Me is methyl;

(4) again the penultimate compound of formula 16 may be treated at reflux with an acidic medium such as 6N HCl to obtain the desired compound of the formula

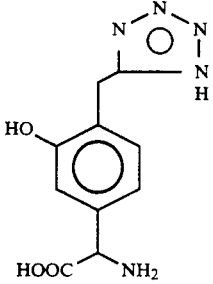

I$_4$

These reactions for compounds I$_1$, I$_2$, I$_3$, and I$_4$ are summarized in Schemes F, G, and H as follows:

SCHEME F

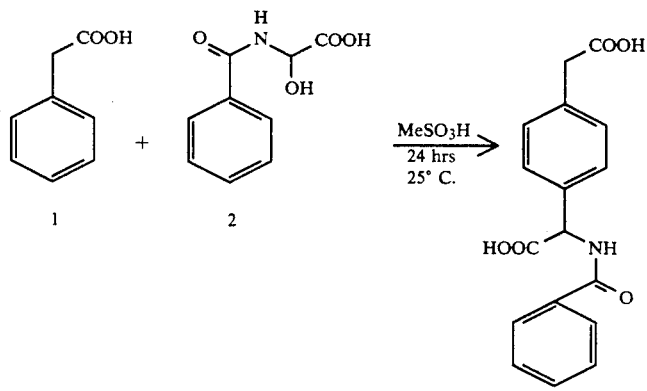

-continued
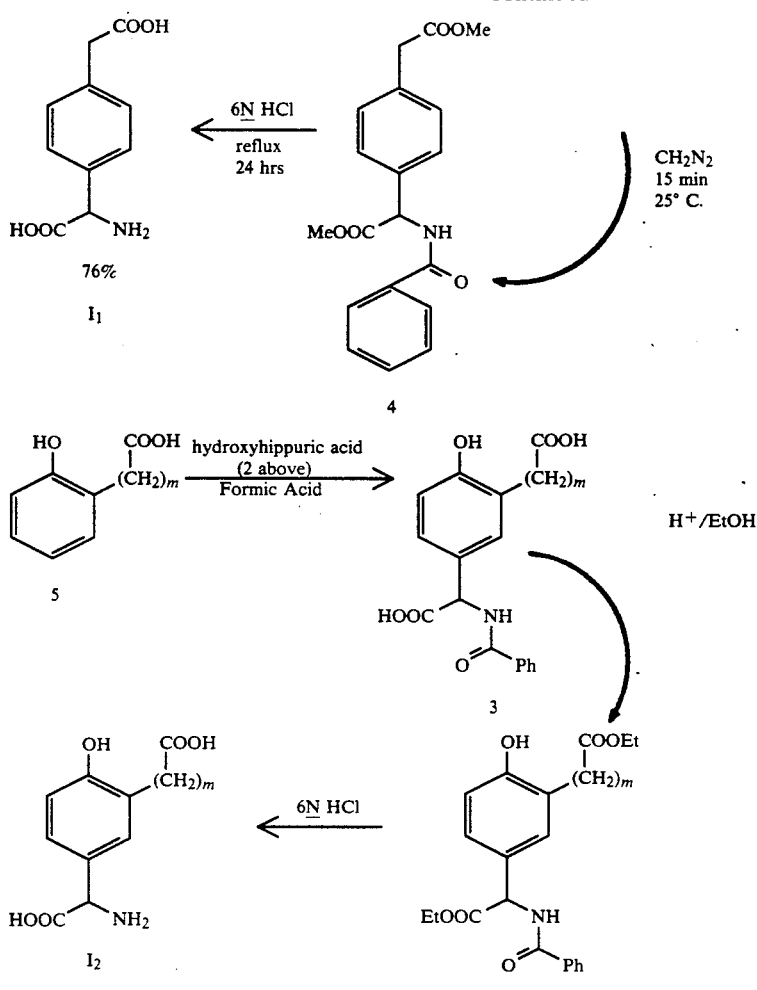
SCHEME G
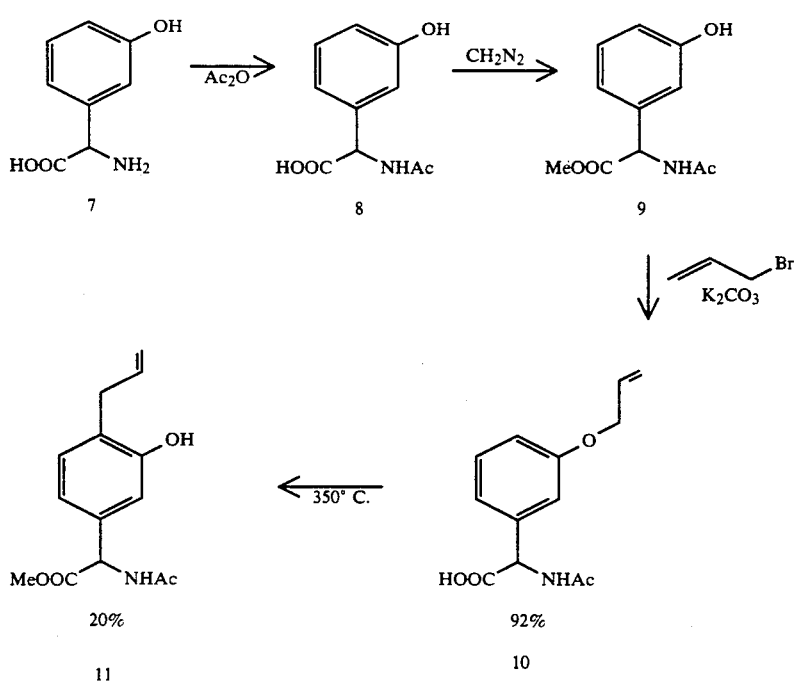

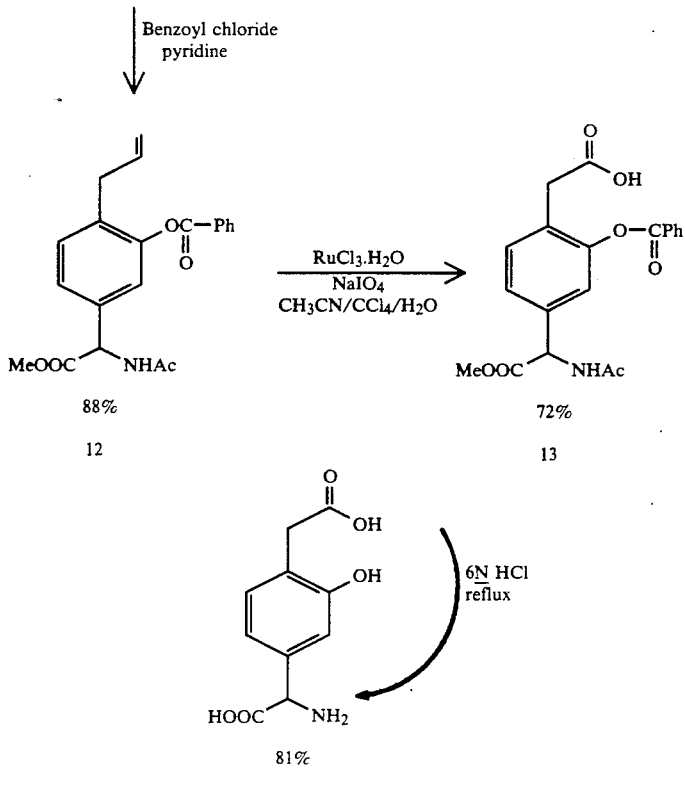

SCHEME H

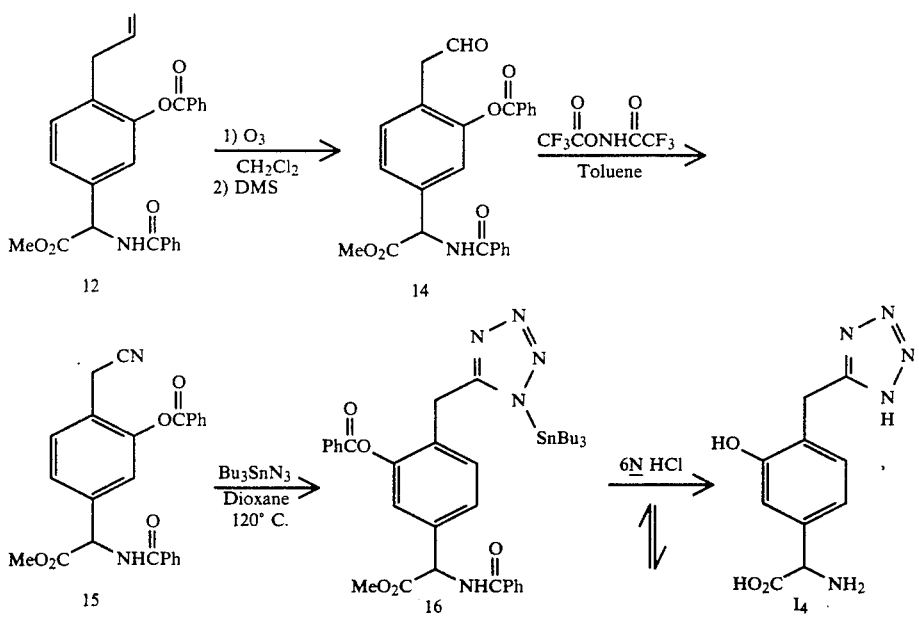

Compounds of the formula I wherein Z is a tetrazolyl may alternatively be prepared by methods analogous to those described in *J. Organometal. Chem.* 33;337-346 (1971).

A process including the following steps (1) to (10) for which the sequence, i.e., order, is critical for the preparations of the compound of the formula I wherein one of $R^3$ and $R^4$ is hydrogen and the other is an OH in a position ortho to the group containing a $PO_3H_2$ that is para to the amino acid containing group comprises (1) treating a compound of the formula

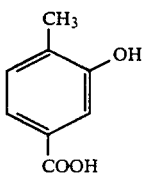

17 with CH₂H₂ to esterify the COOH for protecting it, yielding a compound of the formula

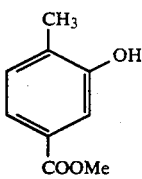
18 wherein Me is methyl;

(2) treating the compound of the formula 17 with a trialkylsilyl halide such as tert-butyldimethylsilyl chloride, trimethylsilyl chloride or dimethylthexylsilyl chloride, preferably tert-butyldimethylsilyl chloride in the presence of a trialkylamine such as triethylamine at room temperature in a solvent such as methylenechloride to obtain a compound of the formula

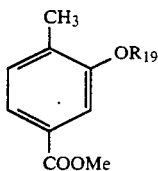
19 wherein Me is methyl and $R_{19}$ is corresponding alkylsilyl (this step introduces a blocking group to hinder ring bromination in the following step);

(3) treating the compound of formula 19 with a free radical halogenating reagent such as N-bromosuccinamide in the presence of a free radical catalyst such as AIBN (azabisisobutyronitrile) in a solvent system such as carbontetrachloride near a source of light such as a high intensity light bulb to obtain the compound of the formula

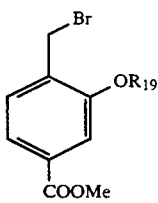
20 wherein Me is methyl and $R_{19}$ is the corresponding alkylsilyl group as above;

(4) treating the compound of formula 20 with a solution of a hydride reducing agent such as lithium aluminum hydride, sodium borohydride, or diisobutyl-aluminum hydride or the like, preferably diisobutyl aluminum hydride in a solvent system such as tetrahydrofuran, diethylether or toluene or the like, at about −78° C. followed by rapid addition of a saturated aqueous potassium-sodium tartrate solution to the reaction mixture at −78° C. to avoid decomposition of the product so there is obtained the compound of the formula

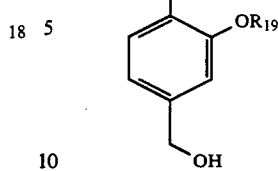
21 wherein Me is methyl and $R_{19}$ is the corresponding alkylsilyl as set out above;

(5) treating the compound of the formula 21 with a trialkyl silyl halide such as tert-butyldimethylsilyl chloride, trimethylsilyl chloride, dimethylthexysilyl chloride in the presence of a trialkylamine such as triethylamine and an amine containing catalyst such as N,N-dimethylaminopyridine at room temperature in a solvent such as methylene chloride to obtain a compound of the formula

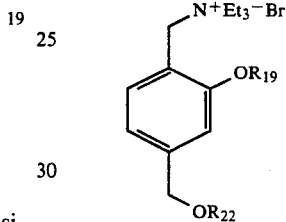
22 wherein Me is methyl, Et is ethyl, and $R_{19}$ and $R_{22}$ are respective corresponding alkylsilyl;

(6) treating the compound of the formula 22 with a trialkylphosphite such as triethylphosphite at about 75° C. to 150° C. preferably at 114° C. to obtain the compound of the formula

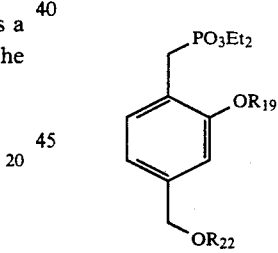
23 wherein Me is methyl, Et is ethyl, and $R_{19}$ and $R_{22}$ are corresponding alkylsilyl;

(7) treating the compound of the formula 23 with a dilute aqueous acid, preferably 1N HCl, in a solvent such as methanol or ethanol at about −20° C. to 20° C., preferably 0° C., to obtain the compound of the formula

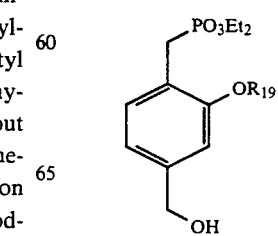
24 wherein Me is methyl, Et is ethyl, and $R_{19}$ is the corresponding alkylsilyl and set out above;

(8) treating the compound of the formula 24 with oxalylchloride and dimethylsulfoxide in the presence of triethylamine in methylenechloride at about $-70°$ C. to $0°$ C. or by other methods known to those skilled in the art to obtain the compound of the formula

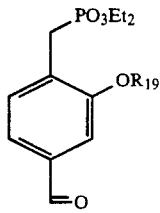   25 wherein Me is methyl, Et is ethyl, and $R_{19}$ is the corresponding alkylsilyl as set out above;

(9) treating the compound of the formula 25 with zinc iodide and a trialkylsilylcyanide such as trimethylsilylcyanide at room temperature in a solvent such as methylenechloride followed by treatment with methanol saturated with ammonia gas with heating to about $40°$ C. to obtain the compound of the formula 9

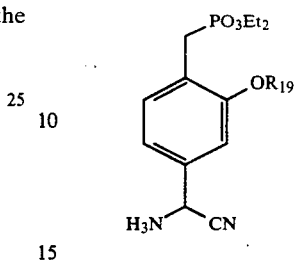   26 wherein Me is methyl, Et is ethyl, and is the corresponding alkylsilyl as set out above;

(10) the compound of the formula 26 may be deprotected by refluxing in acidic medium such as 6N HCl to obtain the compound of the formula

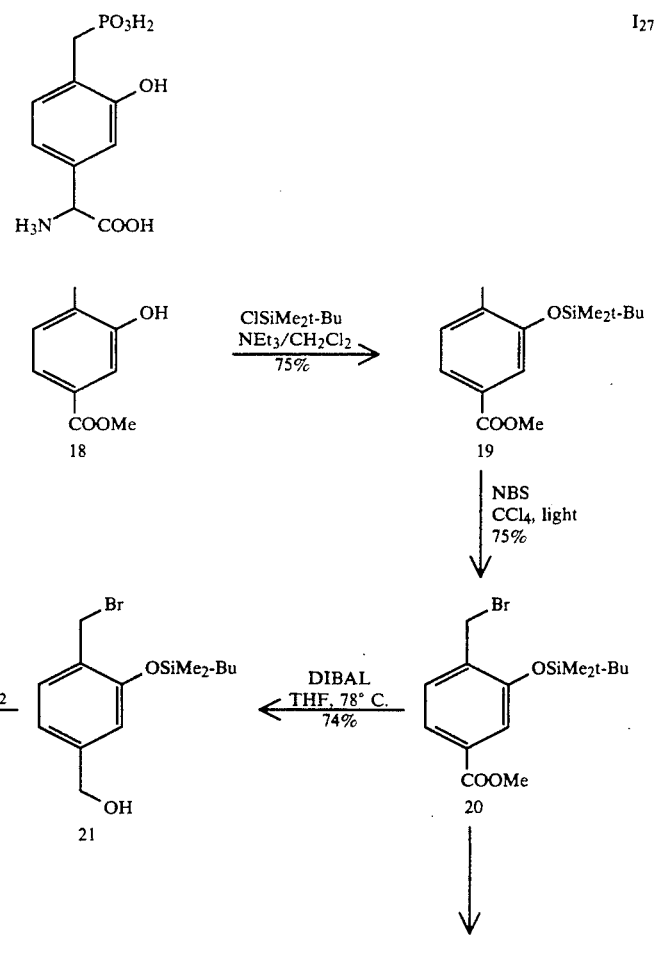

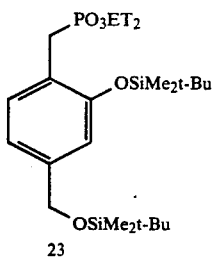 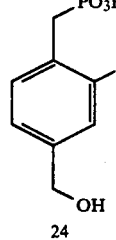 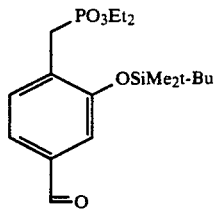

-continued

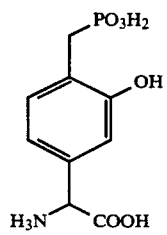 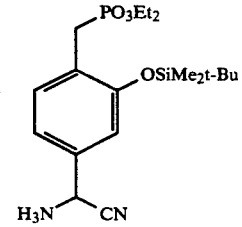

Finally, the compounds of formula IC and IE are prepared from the compounds of the formula IA, IB or ID having corresponding substituents using methods analogous either to those described in U.S. Pat. No. 4,761,405 by $RhCl_3 \cdot 3H_2O$ in the presence of $NaBH_4$ in ethanol at about 30° C. or, in the alternative, by hydrogenation with about 50 psi of hydrogen in methanol or acetic acid using a 10% rhodium on carbon catalyst. Although final stereochemistry is assumed to be predominantly cis, the trans isomers are also within the scope of the invention.

DETAILED DESCRIPTION OF THE INVENTION

In the compounds of formula I the term "lower alkyl" is meant to include a straight or branched alkyl group having one to four carbon atoms, such as, for example, methyl, ethyl, propyl, or butyl, and isomers thereof.

Pharmaceutically acceptable labile ester residues within the context of the present invention represents an ester residue of the esterified carboxy group $I_a$ or "esterified phosphono" group $I_b$ above, preferably a carboxylic acid or phosphono acid prodrug ester that may be convertible under physiological conditions to free carboxy or phosphono acid groups.

That is, the pharmaceutically acceptable esterified carboxy of the group $I_a$ preferably represent e.g., lower alkoxycarbonyl; (amino, mono-,or di-lower alkylamino)- substituted straight chain lower alkoxycarbonyl, carboxy substituted lower alkoxycarbonyl, e.g., α-carboxy-substituted lower alkoxycarbonyl; lower alkoxycarbonyl-substituted lower alkoxycarbonyl, e.g., α-lower alkoxycarbonyl-substituted lower alkoxycarbonyl; aryl-substituted lower alkoxycarbonyl, e.g., unsubstituted or substituted benzyloxyoarbonyl or pyridylmethoxycarbonyl; lower alkanoyloxy-substituted methoxycarbonyl, e.g., pivaloyloxymethoxycarbonyl; (lower alkanoyloxy or lower alkoxy)-substituted lower alkoxymethoxycarbonyl; bicyclo[2.2.1] heptyloxycarbonyl-substituted methoxycarbonyl, e.g. bornyloxycarbonyl-methoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl; e.g., 1-(methoxy- or ethoxycarbonyloxy)-ethoxycarbonyl.

Most preferred prodrug esters are e.g., the straight chain $C_{1-4}$-alkyl esters, e.g., ethyl; the lower alkanoyloxymethyl esters, e.g., pivaloyloxymethyl; the di-lower alkylamino-straight chain $C_{2-4}$-alkyl esters, e.g., 2-diethyl-aminoethyl; the pyridylmethyl esters, e.g., 3-pyridylmethyl.

The labile amide residues of either the carboxy or phosphono substituent may include those amides known by artisans to be useful as prodrugs.

Lower alkoxy is -O-alkyl or of from one to four carbon atoms as defined above for "lower alkyl".

Lower alkylthio is -S-alkyl of from one to four carbons.

Appropriate compounds of formula I are useful in the free base form, in the form of base salts where possible, and in the form of acid addition salts. The three forms are within the scope of the invention. In practice, use of salt form amounts to use of the base form. Pharmaceutically acceptable salts within the scope of the invention are those derived from mineral acids such as hydrochloric acid and sulfuric acid; and organic acids such as ethanesulfonic acid, benzene-sulfonic acid, p-toluenesulfonic acid, and the like, giving the hydrochloride, sulfonate, ethanesulfonate, benzenesulfonate, p-toluenesulfonate, and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-,di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66(1):1-19 (1977).)

The acid addition salts of said basic compounds are prepared either by dissolving the free base of compound I in aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention contain one or more asymmetric carbon atoms. Thus, the invention includes the individual stereoisomers, and mixtures thereof. The individual isomers may be prepared or isolated by methods known in the art.

One of skill in the art would recognize variations in the sequence and would recognize appropriate reaction conditions from analogous reactions which may be appropriately used in the processes to make the compounds of formula I herein. Further, the starting materials are known or can be prepared by known methods.

Under certain circumstances it is necessary to protect the nitrogen atom of intermediates in the above noted process with suitable protecting groups which are known. Introduction and removal of such suitable nitrogen protecting groups are well-known in the art of organic chemistry; see for example, "Protective Groups in Organic Chemistry," J. F. W. McOmie, ed., (New York, 1973), pages 43 ff, 95 ff, J. F. W. McOmie, *Advances in Organic Chemistry* 3:191-281 (1963); R. A. Borssona, *Advances in Organic Chemistry* 3:159-190 (1963); and J. F. W. McOmie, *Chem. & Ind.* 603 (1979).

In the process described herein for the preparation of compounds of this invention the requirements for protective groups are generally well recognized by one skilled in the art of organic chemistry, and accordingly the use of appropriate protecting groups is necessarily implied by the processes of the charts herein, for example, the protecting groups must be stable to the conditions of the processes, although not expressly illustrated.

Starting materials for the processes described above are known or can be prepared by known processes.

The products of the reactions described herein are isolated by conventional means such as extraction, distillation, chromatography, and the like.

The salts of the compounds of formula I described above are prepared by reacting the appropriate base or acid with a stoichiometric equivalent of the compounds of formula I, respectively, to obtain pharmaceutically acceptable salts thereof.

The preferred compounds of the present invention are of the formula I wherein when the groups $I_a$ to $I_b$ or $I_a$ to $I_c$ are in a meta relationship then n is 1 and m is 1 or 2 and also then n is 2 and m is 0; when the groups $I_a$ to $I_b$ or $I_a$ to $I_c$ are in a para relationship then n is 0 and m is 1; or when the groups $I_a$ to $I_b$ and $I_a$ to $I_c$ are in an ortho relationship then n is 1 and m is 2.

The more preferred compounds of the present invention are of the formula I having the limitations of the preferred compounds but further have $R^3$ and $R^4$ selected from hydrogen or hydroxy, particularly in the position ortho to the substituent having the Z group.

Additionally, the compounds having the limitations of the more preferred compounds and additionally having Z defined as the $COOR^5$ or

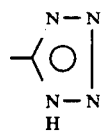

are the most preferred compounds.

The activity of the compounds of the formula I is shown in vitro in an NMDA receptor binding assay based on the use of [$^3$H]CPP as antagonist ligand in a manner essentially as set out by B. E. Murphy, et al, in *J. Pharm. Exp. Ther.* 240:778 (1987). Examples $I_1$, $I_2$, and $I_3$ all exhibit CPP binding activity of $IC_{50}$ better than 100 μM.

The compounds of the present invention can be shown to be antagonists as inhibitors of [$^3$H]TCP tissue binding in an in vitro assay described in *Eur. J. Pharmacol.* 123:467 (1986) and *Neurosci. Lett.* 76:221 (1987) or as inhibitors of glutamate stimulated acetylcholine release from striatal slice preparations as disclosed in *J. Pharm. Exp. Ther.* 240:737 (1987).

In vivo activity for the compounds of the present invention is shown by selected compounds in the assays of EP Publication Number 318935, incorporated herein by reference, which are generally accepted to establish the utility for the treatment of diseases as noted above.

Therefore, the compounds of formula I and their pharmacologically acceptable acid addition salts are effective agents in the prophylaxis and/or therapeutic treatment of disorders responsive to agents which block NMDA receptors, thus forming a further aspect of the present invention in like manner.

For medical use, the amount required of a compound of formula I or pharmacologically acceptable salt thereof (hereinafter referred to as the active ingredient) to achieve a therapeutic effect will, of course, vary both with the particular compound, the route of administration and the mammal under treatment and the particular disorder or disease concerned. A suitable systemic dose of a compound of formula I or pharmacologically acceptable salt thereof for a mammal suffering from, or likely to suffer from any condition as described hereinbefore is in the range 0.01 to 100 mg of base per kilogram body weight, the most preferred dosage being 0.05 to 50 mg/kg of mammal body weight.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by intravenous infusion and repeated administrations, parenterally or orally, as considered appropriate.

While it is possible for an active ingredient to be administered alone, it is preferable to present it as a formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

Formulations suitable for parenteral administration conveniently comprise a sterile aqueous preparation of the active ingredient which is preferably isotonic with the blood of the recipient.

Formulations suitable for nasal or buccal administration, (such as self-propelling powder dispensing formulations described hereinafter), may comprise 0.1 to 20% w/w, for example 2% w/w of active ingredient.

The formulations, for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

So the pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose, and/or glycine; b) lubricants, e.g. silica, talcum, stearic acid, its magnesium or calcium salt, and/or polyethyleneglycol; for tablets also; c) binders e.g. magnesium aluminum silicate, starch paste, gelatin, tragacanth, methylcellulose, sodium carboxymethyl-cellulose and/or polyvinylpyrrolidone; if desired d) disintegrants, e.g. starches, agar, alginic acid, or its sodium salt, or effervescent mixtures; and/or e) absorbents, colorants, flavors, and sweeteners. Injectable compositions are preferably aqueous isotonic solutions or suspensions, and suppositories are advantageously prepared from fatty emulsions, or suspensions. Said compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and contain about 0.1 to 75%, preferably about 1 to 50%, of the active ingredient.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Finally, the present invention is a method of prophylactic or therapeutic treatment of cerebral ischemia, cerebral infarction, thromboembolic or hemorrhagic stroke, cerebral vasospasm, hypoglycemia, cardiac arrest, status epilepticus, schizophrenia, epilepsy, neurodegenerative disorders, Alzheimer's disease, Huntington's disease, or risk of cerebrovascular damage which comprises administering an antagonist effective amount for excitatory amino acid receptors of a compound of the formula I in unit dosage form.

The invention is further elaborated by the representative examples as follows. Such examples are not meant to be limiting.

EXAMPLES

Preparation I

α-[(Phenylcarbonyl)amino]-1,4-benzenediacetic acid

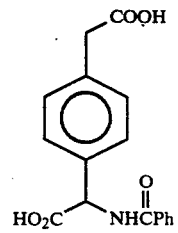

A solution of phenyl acetic acid (10.0 g, 73.5 mmol) in 25 ml methanesulfonic acid is treated with α-hydroxyhippuric acid (3.58 g, 18.4 mmol) and the resulting solution stirred at room temperature for 24 hours. The reaction mixture is poured onto ice (200 g) and the product extracted into ethyl acetate (3×200 ml). The combined organic layers are dried (Na$_2$SO$_4$) and concentrated. The residue is recrystallized from THF/diisopropyl ether. A tan solid which is α-[(phenylcarbonyl)amino]-1,4-benzenediacetic acid is obtained (1.5 g, 26%), mp 180°–220° C.

Preparation 2

Dimethyl α-[(phenylcarbonyl)amino]-1,4-benzenediacetate

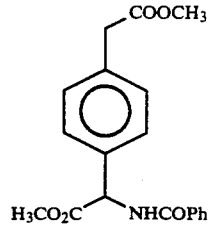

4

A solution of α-[(phenylcarbonyl)amino]-1,4-benzenediacetic acid (1.31 g, 4.19 mmol) from the Preparation I above in 150 ml of THF is treated with a solution of diazomethane in ether until a persistent yellow color develops. The resulting solution is concentrated and the residue purified by silica gel chromatography (EtOAc). A waxy yellow solid of dimethyl α-[(phenylcarbonyl)amino]-1,4-benzenediacetate is obtained (1.30 g, 93%), mp 102–112 C.°.

Anal. calcd for C$_{19}$H$_{19}$NO$_5$:
C, 66.85; H, 5.61; N, 4.10.
Found: C, 66.81; H, 5.71; N, 4.00.

Example 1

1,4-Benzenediacetic acid, α-amino-, (±)

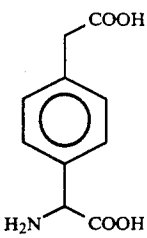

A solution of dimethyl α-[(phenylcarbonyl)amino]-1,4-benzenediacetate (1.00 g, 2.90 mmol) from the Preparation 2 above in 20 ml of 6N HCl is heated at reflux under N₂ for 19 hours. The reaction mixture is cooled and extracted with a 1:1 toluene/ether solution (2×40 ml). The aqueous layer is concentrated and the residue dissolved in H₂O (10 ml) and freeze-dried. A solid, 1,4-benzenediacetic acid, a-amino-, (±) is obtained (0.72 g, 76%), mp 205° C.

Anal. calcd. for $C_{10}H_{11}NO_4.2.2NH_4Cl$:

C, 37.05; H, 6.09; N, 13.61.

Found: C, 37.00; H, 6.36; N, 13.58.

Preparation 3

4-Hydroxy-α-[(phenylcarbonyl)amino]-1,3-benzenediacetic acid 1-ethyl ester

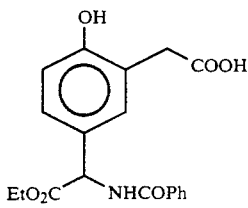

A solution of 2-hydroxyphenylacetic acid (10.0 g, 66 mmol) and a-hydroxyhippuric acid (3.2 g, 16 mmol) in 50 ml formic acid is stirred at 0° C. for two hours. The solution is warmed to room temperature and allowed to stir for an additional 44 hours. The resulting solution is poured into 400 ml of ice water. The solid which formed is collected by suction filtration. The solid is dissolved in EtOH (150 ml) and sulfuric acid (5 ml) is added. The resulting solution is heated to reflux for 16 hours. The reaction mixture is cooled and poured into H₂O (50 ml). The mixture is extracted into ethyl acetate, dried (Na₂SO₄) and concentrated. The residue is purified by silica gel chromatography (80% EtOAc/Heptane). A white solid, 4-hydroxy-α-[(phenylcarbonyl)amino]-1,3-benzenediacetic acid 1-ethyl ester is obtained (0.35 g, 5%).

Example 2

α-Amino-4-hydroxy-1,3-benzenediacetic acid

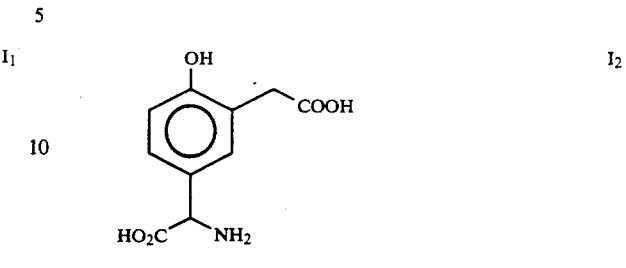

A solution of 4-hydroxy-α-[(phenylcarbonyl)amino]-1,3-benzenediacetic acid 1-ethyl ester from Preparation 3 above (0.50 g, 1.4 mmol) is dissolved in 15 ml of 3N HCl and the resulting solution heated at reflux for 24 hours. The reaction mixture is cooled to room temperature, filtered, and concentrated. The residue is dissolved in 1N HCl (25 ml) and extracted with 50% EtzO/toluene (2×25 ml). The aqueous layer is concentrated and dissolved in 10 ml H₂O. The solution is freeze-dried. An orange solid is obtained (0.25 g, 73%), mp 180–210° C., softens and foams.

Anal.: Calcd for $C_{10}H_{11}NO_5 \cdot 0.40\ C_7H_6O_2 \cdot$
2.6 HCl ·0.67 H₂O

C, 39.89; H, 4.58; N, 3.69.

Found: C, 39.89; H, 4.59; N, 3.69.

Preparation 4

Methyl α-(acetylamino)-3-hydroxybenzeneacetate

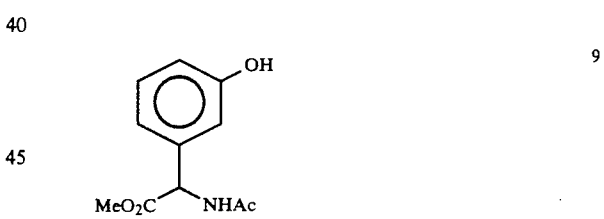

A solution of m-hydroxyphenylglycine (25.0 g, 0.15 mol) and NaOH (16 g) in 40 ml H₂O is cooled to 0° C. and acetic anhydride (12.5 g, 0.22 mol) is added over a one-hour period. Additional NaOH (20 g) in 20 ml H₂O is added followed by acetic anhydride (12.5 g, 0.22 mol). The resulting solution is extracted with EtOAc (6×100 ml). The combined organic phases are dried (MgSO₄) and concentrated. The residue (30 g) is dissolved in MeOH 200 ml and treated with a solution of diazomethane in ether until esterification was complete. The resulting solution is concentrated. A viscous oil of methyl α-(acetyl-amino)-3-hydroxybenzeneacetate is obtained (32.0 g). This material is used directly in the preparation of methyl α-(acetylamino)-3-(2-propenoxy)benzeneacetate hereinafter.

Preparation 5

Methyl α-(acetylamino)-3-(2-propenoxy)benzeneacetate

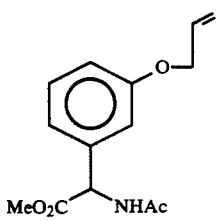

10

A suspension of the formula 9 from Preparation 4 (32.0 g, 0.143 mol), allyl bromide (17.6 g, 0.145 mol), and potassium carbonate (21.5 g, 0.156 mol) in 300 ml of acetone is heated at reflux for 24 hours. The reaction mixture is cooled, concentrated and the residue treated with EtOAc and H₂O. The organic phase is isolated, dried (MgSO₄) and concentrated. The residue (32 g) is crystallized from hot heptane/ethyl acetate to afford pink needles of the formula 10 above (25.0 g, 66%), mp 87° C.

Preparation 6

Methyl α-(acetylamino)-3-hydroxy-2-(2-propenyl)-benzeneacetate and Methyl α-(acetylamino)-3-hydroxy-4-(2-propenyl)benzeneacetate

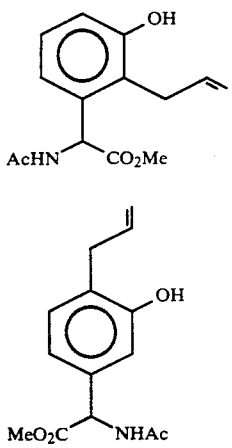

11a

11

A solution of methyl α-(acetylamino)-3-(2-propenoxy)benzeneacetate from Preparation 5 above (8.0 g, 32 mmol) in 15 g of p-dichlorobenzene is heated at 350° C. for 16 hours in a sealed tube. The reaction mixture is cooled and the contents of the tube are purified by silica gel chromatography, eluting with CHCl₃ to remove the p-dichlorobenzene and then with 5% MeOH-CHCl₂ to remove the rearrangement products (methyl α-(acetylamino)-3-hydroxy-2-(2-propenyl) benzeneacetate, methyl α-(acetylamino)-3-hydroxy-4-(2-propenyl)-benzeneacetate). The rearrangement products (a 1:1 mixture of methyl α-(acetylamino)-3-hydroxy-2-(2-propenyl)-benzeneacetate, methyl α-(acetylamino)-3-hydroxy-4-(2propenyl)benzeneacetate) are separated by silica gel chromatography (Chromatotron/EtOAc). Recrystallization from diisopropylether/THF gives the compound of methyl α-(acetylamino)-3-hydroxy-4-(2-propenyl)benzeneacetate above (2.60 g, 33%) as a white solid, mp 143°-145° C.

Preparation 7

Methyl α-(acetylamino)-3-[(phenylcarbonyl)oxy]-4-(2propenyl)-benzeneacetate

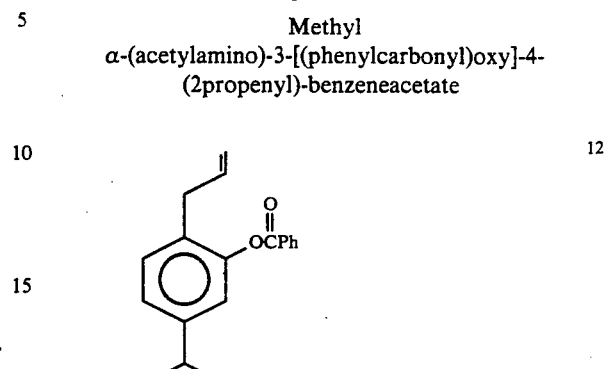

12

A solution of methyl α-(acetylamino)-3-hydroxy-4-(2-propenyl)benzeneacetate from Preparation 6 (1.5 g, 5.7 mmol) in CHCl₃ (20 ml) and Et₃N (1 ml) is treated with benzoyl chloride (1.0 g, 7.1 mmol). The resulting solution is stirred at room temperature for 4.5 hours. The reaction mixture is concentrated and the residue partitioned between EtOAc and saturated aqueous NaHCO₃. The organic phases are combined, dried (MgSO₄) and concentrated. The residue is purified by silica gel chromatography (50% EtOAc/Heptane). An oil of methyl α-(acetylamino)-3-[(phenylcarbonyl)oxy]-4-(2-propenyl)benzeneacetate is obtained (2.1 g, quantitative).

Preparation 8

α'-(Acetylamino)-3-[(phenylcarbonyl)oxy]-1,4-benzenediacetic acid 4-methyl ester

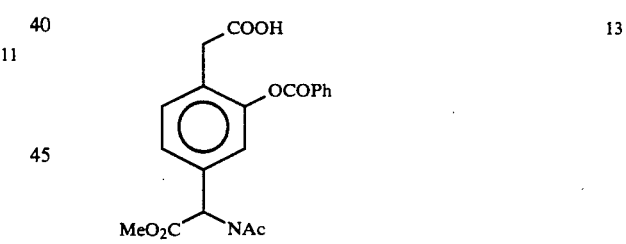

13

A mixture of methyl α-(acetylamino)-3-[(phenylcarbonyl)oxy]-4-(2-propenyl)benzeneacetate from Preparation 7 above (0.6 g, 1.6 mmol), sodium metaperiodate (1.4 g, 6.7 mmol) and RuCl₃·H₂O (10 mg, 0.05 mmol) in a H₂O (8 mL), CH₃CN (5 ml), CCl₄ (5 ml) is stirred rapidly at 25° C. for seven hours. The reaction mixture is poured into 50 ml EtOAc and 50 ml (1N HCl). The organic phase is separated and the aqueous phase extracted with EtOAc (2×25 ml). The combined organic phases are washed with H₂O (25 ml, brine (25 ml) and NaHCO₃ (2×50 ml). The combined NaHCO₃ washes are acidified with 1N HCl and extracted with EtOAc (3×70 ml). The combined organic phases are dried (MgSO₄) and concentrated. The residue is dissolved in ether (20 ml) and concentrated. A foamy white solid of α'-(acetylamino)-3-[(phenylcarbonyl)oxy]-1,4-benzenediacetic acid 4-methyl ester above is obtained (0.39 g, 65%), mp 78-82° C. (dec).

Example 3

1,4-Benzenediaoetic acid,
α-amino-2-hydroxy-,-monohydrochloride, (±)

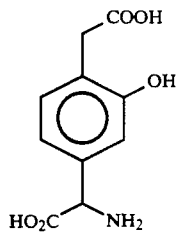

A solution of α'-(acetylamino)-3-[(phenyl-carbonyl)oxy]-1,4-benzenediacetic acid 4-methyl ester from Preparation 8 above (0.39 g, 1.04 mmol) in 60 ml of 6N HCl is heated at reflux for 24 hours. The reaction mixture is cooled and extracted with 1:1 toluene/ether (3 × 10 ml). The aqueous phase is decolorized with charcoal, filtered and concentrated. The residue is taken up in H₂O and freeze dried. A white solid of 1,4-benzenediacetic acid, α-amino-2-hydroxy-,monohydrochloride, (±) is obtained (0.185 g, 64%), mp 125° (softened).

Anal. Calcd for $C_{10}H_{11}NO_5 \cdot HCl \cdot H_2O$
C, 42.70; H, 5.04; N, 4.98; Cl, 13.11.
Found: C, 42.70: H, 4.55; N, 4.50; Cl, 13.11.

Preparation 9

Methyl 4-(2-oxoethyl)-α-[(phenylcarbonyl)amino]-3-[(phenyl-carbonyl)oxy]benzeneacetate

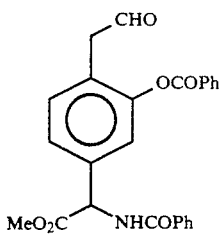

A solution of α'-(acetylamino)-3-[(phenylcarbonyl)oxy]-1,4-benzenediacetic acid 4-methyl ester from Preparation 7 above in dichloromethane at −78° C. is treated with ozone until starting material is consumed. The reaction mixture is purged with oxygen and warmed to 0° C. The reaction mixture is treated with dimethyl sulfide (3 eq) and is warmed to room temperature. The reaction mixture is concentrated and the product, methyl 4-(2-oxoethyl)-α-[(phenylcarbonyl)amino]-3-[(phenylcarbonyl)oxy]benzeneacetate, is isolated by silica gel chromatography.

Preparation 10

Methyl 4-(cyanomethyl)-α-[(phenylcarbonyl)amino]-3-[(phenylcarbonyl)oxy]benzeneacetate

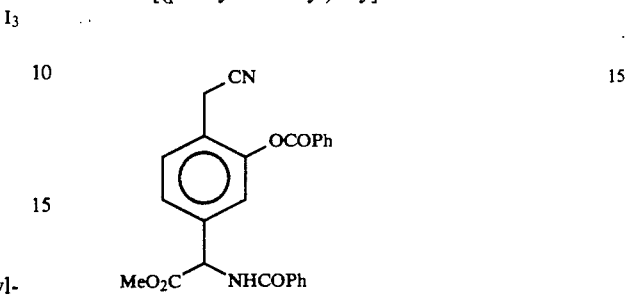

A solution of methyl 4-(2-oxoethyl)-α-[(phenylcarbonyl)amino]-3-[(phenylcarbonyl)oxy]benzeneacetate from Preparation 9 above in toluene containing pyridine (2.3 eq) is treated with O,N-bistrifluoroacetyl hydroxyl amine (1.0 eq). The resulting solution is allowed to stir until no starting material remains. The reaction mixture is washed with saturated eq NaHCO₃ solution, dried (MgSO₄), and concentrated. The product of the formula 15 above is purified by silica gel chromatography.

Preparation 11

Methyl α-(phenylcarbonyl)amino]-3-[(phenylcarbonyl)-oxy]-4-[[2-(tributylstannyl)-1H-tetrazol-5-yl]methyl]-benzeneacetate

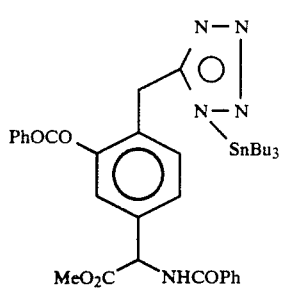

A solution of methyl 4-(cyanomethyl)-α-[(phenylcarbonyl)amino]3-[(phenylcarbonyl)oxy]benzeneacetate from Preparation 10 above in dioxane is treated with tri-n-butyltinazide (2.5 eq). The resulting solution is heated at 120° C. until no starting material remains. The reaction mixture is concentrated and the product of methyl α-[(phenylcarbonyl)amino]-3-[(phenylcarbonyl)oxy]-4-[[2-(tributylstannyl)-1H-tetrazol-5-yl]methyl]-benzeneacetate is purified by silica gel chromatography.

Example 4

α-Amino-3-hydroxy-4-(1H-tetrazol-5-ylmethyl)benzeneacetic acid

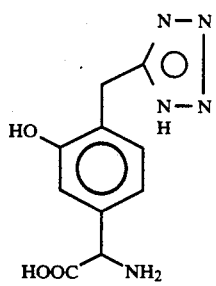

A solution of methyl α-[(phenylcarbonyl)amino]-3-[(phenylcarbonyl)-oxy]-4-[[2-(tributylstannyl)-1H-tetrazol-5-yl]methyl]benzeneacetate from the Preparation 11 above in 6N HCl is heated at reflux until consumed. The reaction mixture is cooled to room temperature and extracted with 1:1 ether/toluene. The aqueous phase is concentrated to give the product of α-amino-3-hydroxy-4-(1H-tetrazol-5-ylmethyl)-benzeneacetic acid.

Preparation 12

Methyl 3-hydroxy-4-methylbenzoate

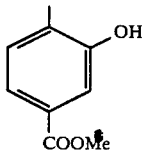

A solution of 3-hydroxy-4-methylbenzoic acid (26.1 g, 0.17 mol) in 200 mL of diethylether is treated with a solution of diazomethane in ether until a persistent yellow color develops. The resulting solution is stirred for 24 hours. The resulting solution is concentrated and the residue is crystallized from CH₂Cl₂. A white solid which is methyl 3-hydroxy-4-methylbenzoate is obtained (26.5 g, 93%).

Preparation 13

Methyl 3-[[(1,1-dimethylethyl)dimethylsilyl]oxy]-4-methylbenzoate

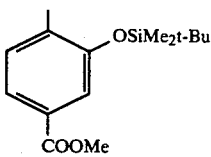

A solution of 3-hydroxy-4-methylbenzoate (5.55 g, 33 mmol) from Preparation 12, tert-butyldimethylsilyl chloride (7.6 g, 50 mmol), and triethylamine (14 mL, 100 mmol) in 50 mL CH₂Cl₂ is stirred at room temperature for 24 hours. An additional 25 mL of CH₂Cl₂ is added and washed with water. The organic layer is dried (MgSO₄) and concentrated. The product is isolated by silica gel chromatography (100% CH₂Cl₂). An oil of methyl 3-[[(1,1-dimethylethyl)-dimethylsilyl]oxy]-4-methylbenzoate is obtained (9.05 g, 97%).

Preparation 14

Methyl 4-(bromomethyl)-3-[[(1,1-dimethylethyl)-dimethylsilyl]oxy]benzoate

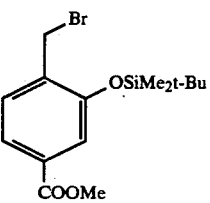

A solution of methyl 3-[(1,1-dimethylethyl)dimethylsilyl]oxy-4-methylbenzoate (11.36 g, 40.5 mmol) from Preparation 13, N-bromosuccinimide (6.5 g, 36.5 mmol), and AIBN 100 mg, 0.61 mmol) in CCl₄. The reaction mixture is stirred at room temperature for 1 hour while exposed to a high intensity light bulb. The precipitate is removed by suction filtration and the filtrate is concentrated. The residue is purified by silica gel chromatography (1% tetrahydrofuran/petroleum ether). An oil of methyl 4-(bromomethyl)-3-[[(1,1-dimethylethyl)-dimethylsilyl]oxy]benzoate is obtained 99.87 g, 75%).

Preparation 15

4-(Bromomethyl)-3-[[(1,1-dimethylethyl)dimethylsilyl]oxy]benzenemethanol

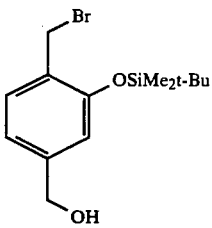

A solution of methyl 4-(bromomethyl)-3-[[(1,1-dimethylethyl)dimethylsilyl]oxy]benzoate (1.59 g, 4.2 mmol) from Preparation 14 in THF 15 mL), cooled to −78° C. is treated with diisobutylaluminum hydride (1M, 10.4 mL, 10.4 mmol). The reaction mixture is stirred for 3.5 hours. The reaction mixture is treated with 20 mL of a saturated potassium-, sodium-tartrate solution, diethylether (200 mL) and is allowed to warm to room temperature. The organic phase is separated, dried (MgSO₄), and concentrated. The residue is purified by silica gel chromatography (1% MeOH/CH₂Cl₂). An oil of 4-(bromomethyl)-3-[[(1,1-dimethylethyl)dimethylsilyl]oxy]benzenemethanol is obtained (1.02 g, 74%).

Preparation 16

2-[[(1,1-dimethylethyl)dimethylsilyl]oxy]-4-[[[(1,1-dimethylethyl)dimethylsilyl]oxy]methyl]-N,N,N-triethylbenzenemethanaminium bromide

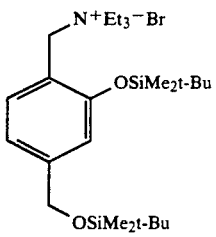

A mixture of 4-(bromomethyl-3-[[(1,1-dimethylethyl)dimethylsilyl]oxy]benzenemethanol (6.35 g, 19.2 mmol) from Preparation 15, tert-butyldimethylsilyl chloride (4.3 g, 28.8 mmol), triethylamine (5.3 mL, 38.3 mmol), and dimethylaminopyridine (90 mg) in dichloromethane (50 mL) is stirred at room temperature for 24 hours. Dichloromethane (1 L) is added and the organic phase washed with H₂O 100 mL). The organic phase is dried (MgSO₄) and concentrated. The residue is purified by silica gel chromatography (2.5% MeOH/CH₂Cl₂ followed by 5% MeOH/CHCl₂). A yellow-orange solid of 2-[[(1,1-dimethylethyl)dimethylsilyl]-oxy]-4-[[[(1,1-dimethylethyl) dimethylsilyl]oxy]-methyl]-N,N,N-triethylbenzenemethanaminium bromide is obtained (7.68 g, 73%).

Anal. Calc. for $C_{26}H_{52}NO_2Si_2Br$
C, 57.11; H, 9.59; N, 2.56; Br, 14.61.
Found: C, 57.11; H, 9.50; N, 2.44; Br, 14.32.

Preparation 17

Diethyl [[2-[[(1,1-dimethylethyl)dimethylsilyl]oxy]-4-[[[(1,1-dimethylethyl)dimethylsilyl]oxy]methyl]-phenyl]methyl]phosphonate

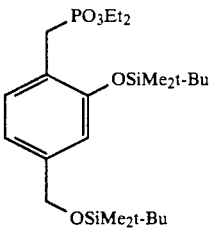

A mixture of 2-[[(1,1-dimethylethyl)dimethylsilyl]xoy]-4-[[[(1,1-dimethylethyl) dimethylsilyl]oxy]-methyl]-N,N,N-triethylbenzenemethanaminium bromide (2.25 g, 4.12 mmol) from Preparation 16 and triethylphosphite (1.4 mL, 8.23 mmol) is heated under an aspirator vacuum to 144° C. for 3.5 hours. The residue is purified by silica gel chromatography (2.5% MeOH/CH₂Cl₂ followed by 5% MeOH/CH₂Cl₂). A colorless oil of diethyl [[2-[[(1,1-dimethylethyl) dimethylsilyl]oxy]-4-[[[(1,1-dimethylethyl)dimethylsilyl]oxy]methyl]-phenyl]methyl]phosphonate is obtained 1.51 g, 73%).

Preparation 18

Diethyl [[2-[[(1,1-dimethylethyl)dimethylsilyl]oxy]-4-(hydroxymethyl)phenyl]methyl]phosphonate

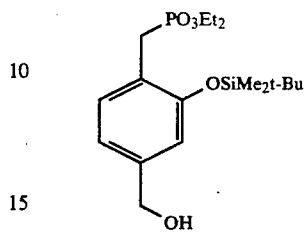

A solution of diethyl [[2-[[(1,1-dimethylethyl)dimethylsilyl]oxy]-4-[[[(1,1-dimethylethyl)dimethylsilyl]oxy]methyl]phenyl]methyl]phosphonate (3.23 g, 6.4 mmol) from Preparation 17 in ethanol (30 mL) at 0° C. is treated with 1 mL of 1N HCl. The mixture is stirred at 0° C. for 2 hours. The solution is poured onto 500 mL EtOAc and water (50 mL). The organic phase is separated, dried (MgSO₄), and concentrated. The residue is purified by silica gel chromatography (2.5% MeOH/CH₂Cl₂ followed by 5% MeOH/CH₂Cl₂). A colorless oil of diethyl [[2-[[(1,1-dimethylethyl)dimethylsilyl]oxy]-4-(hydroxymethyl)phenyl]methyl]phosphonate is obtained (1.73 g, 69%).

Preparation 19

Diethyl [[2[[(1,1-dimethylethyl)dimethylsilyl]oxy]-4-formylphenyl]methyl]phosphonate

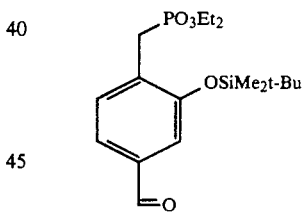

A solution of oxalylchloride (0.6 g, 6.7 mmol) in 20 mL methylene chloride is cooled to −70° C. Dimethylsulfoxide (0.6 mL, 8.4 mmol) is added dropwise. The solution is warmed to −30° C. then cooled to −70° C. A solution of diethyl [[2-[[(1,1-dimethylethyl)dimethylsilyl]oxy]-4-(hydroxymethyl)phenyl]methyl]phosphonate (1.73 g, 4.45 mmol) from Preparation 18 in methylenechloride (15 mL) is added to the reaction mixture. The reaction mixture is stirred for 0.5 hours then warmed to −35° C. Triethylamine (4.7 mL, 33.5 mmol) is added and the mixture allowed to warm to room temperature. Methylenechloride (400 mL) is added and the organic phase is washed with 100 mL H₂O. The organic phase is dried (MgSO₄) and concentrated. The residue is passed through a 200-g silica gel plug using 5% MeOH/CH₂Cl₂ as the eluent. An oil of diethyl [[2-[[(1,1-dimethylethyl)dimethylsilyl]oxy]-4-formylphenyl]methyl]phosphonate is obtained (1.67 g, 97%).

Preparation 20

Diethyl [[4-(aminocyanomethyl)-2-[[(1,1-dimethylethyl)dimethylsilyl]oxy]phenyl]methyl]phosphonate

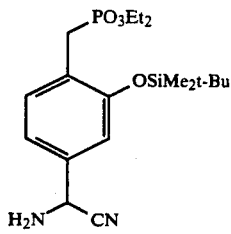

A solution of diethyl [[2-[[(1,1-dimethylethyl)dimethylsilyl]oxy-4-formylphenyl]methyl]phosphonate (1.67 g, 4.32 mmol) from Preparation 19 in $CH_2Cl_2$ (5 mL) is treated with trimethylsilylcyanamide (0.72 mL, 5.4 mmol) and $ZnI_2$ (10 mg). The reaction mixture is stirred at room temperature for 30 minutes. A solution of methanol (20 mL) saturated with ammonia gas is added. The mixture is heated to 45° C. for 3 hours. The reaction mixture is concentrated. The residue is taken up in diethylether and $H_2O$. The organics were separated, dried ($MgSO_4$), and concentrated. The residue is purified by silica gel chromatography (1% $MeOH/CH_2Cl_2$ followed by 2.5% $MeOH/CH_2Cl_2$ followed by 5% $MeOH/CH_2Cl_2$). An oil of diethyl [[4-(aminocyanomethyl)-2-[[(1,1-dimethylethyl)dimethylsilyl]oxy]phenyl]methyl]phosphonate is obtained (600 mg, 34%).

Example 5

(±)-1α-amino-3-hydroxy-4-(phosphonomethyl)-benzeneacetic acid monohydrochloride

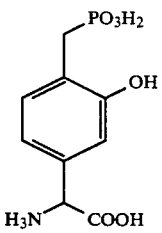

A solution of diethyl [[4-(aminocyanomethyl)-2-[[1,1-dimethylethyl) dimethylsilyl]oxy]phenyl]methyl]-phosphonate from Preparation 20 (600 mg, 1.54 mmol) in 5 mL of 6N HCl is heated to 95° C. for 16 hours. The aqueous phase is concentrated to dryness and the residue is triturated with acetone. The solid was collected by suction filtration and washed with acetone. The solid is dried under vacuum at 100° C. A white solid of (±)-1α-amino-3-hydroxy-4-(phosphonomethyl)-benzeneacetic acid monohydrochloride is obtained (350 mg, 81%).

Anal. Calc. for $C^9H^{12}NO^6P \cdot HCl \cdot NH_4Cl \cdot 1.44 C_3H_6O$
C, 36.80; H, 5.94; N, 6.44; Cl, 16.31.
Found: C, 36.95; H, 5.63; N, 6.69; Cl, 15.08.

We claim:

1. A compound of the formula (IA or IC)

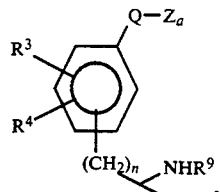

or

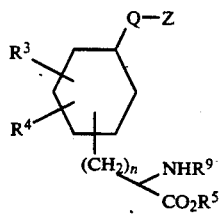

or a pharmaceutically acceptable acid addition, or base salt thereof wherein the group ($I_a$)

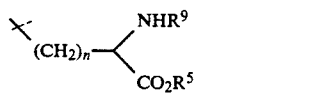

is ortho, meta or para to the group ($I_b$ or $I_d$)

or

wherein
(1) n is 0, 1, or 2;
(2) $R^5$ is independently hydrogen, lower alkyl, lower alkanoyloxymethyl, or di-lower alkylamino-straight chain alkyl of from two to four carbons [or a pharmaceutically acceptable labile ester or amide residue];
(3) $R^3$ and $R^4$ are independently hydrogen, hydroxy, lower alkyl, aryl, aralkyl, lower alkoxy, lower alkylthio, halogen, trifluoromethyl, lower alkoxymethyl or taken together with adjacent ring carbons are —CH=CH—CH=CH—;
(4) $R^9$ is a hydrogen or a protective group;
(5) Q is —$(CH_2)_m$—, —(CH=CH)—, —$CH_2$—(CH=CH)—, or (CH=CH)—$CH_2$—wherein m is 1, 2, or 3;

$Z_a$ or Z are —$CO_2R^{20}$ wherein $R^{20}$ is independently selected from hydrogen, lower alkyl, lower alkenyl, aryl, aryl lower alkyl, lower alkanoyloxymethyl, or di- lower alkylamino-straight chain alkyl of from two to four carbons.

2. A compound of claim 1 which is a compound of the formula I such that (1) when the group $I_a$ is para to the group $I_b$ then (i) n is 0 when m is 1, 2, or 3 or (ii) n is 1 when m is 2 or (2) when the group $I_a$ is meta to the group $I_b$ then (i) n is 0 when m is 1 or 2, or (ii) n is 1 when m is 1 or 2; or (3) when the group $I_a$ is ortho to $I_b$ then n is 1 and m is 1, 2, or 3.

3. A compound of claim 1 having the formula IA wherein $R^3$, $R^4$, $R^5$, $R^9$, $Z_a$, and n are as defined above.

4. A compound of claim 3 wherein $I_a$ is para to $I_b$ and (i) n is 0 and m is 1, 2, or 3 or (ii) n is 1 and m is 2.

5. A compound of claim 3 wherein $I_a$ is meta to $I_b$ and (i) n is 0 and m is 1 or 2, or (ii) n is 1 and m is 1 or 2.

6. A compound of claim 3 wherein $I_a$ is ortho to $I_b$ and n is 1 and m is 1, 2, or 3.

7. A compound of claim 1 having the formula IC wherein $R^3$, $R^4$, $R^5$, $R^9$, Z and n are as defined above.

8. A compound of claim 7 wherein $I_a$ is para to $I_d$ and (i) n is 0 and m is 1, 2, or 3 or (ii) n is 1 and m is 2.

9. A compound of claim 7 wherein $I_a$ is meta to $I_d$ and (i) n is 0 and m is 1 or 2, or (ii) n is 1 and m is 1 or 2.

10. A compound of claim 7 wherein $I_a$ is ortho to $I_d$ and n is 1 and m is 1, 2, or 3.

11. A compound of the formula

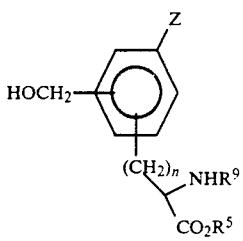

ID or

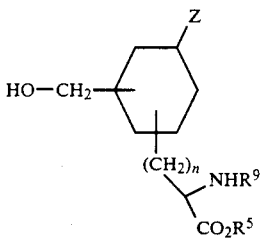

IE wherein Z, n, $R^9$, and $R^5$ are as defined in claim 1.

12. A compound of claim 11 wherein when

1) 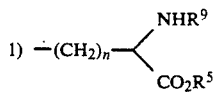

is para to Z then (i) n is 0 and m is 1, 2, or 3; (ii) n is 1 and m is 2;

2) 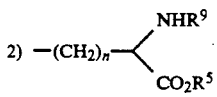

is meta to Z then (i) n is 0 and m is 1 or 2; (ii) n is 1 and m is 1 or 2; or

3) 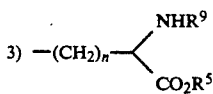

is ortho to Z then n is 1 and m is 1, 2, or 3.

13. A compound of claim 2 wherein $R^5$ is independently hydrogen or lower alkyl.

14. A compound of claim 3 which is (+,−)-α-amino-1,4- benzenediacetic acid.

15. The monohydrochloride salt of the compound of claim 11.

16. A compound of claim 3 which is (+)-α-amino-2-hydroxy-1, 4-benzenediacetic acid.

17. The monohydrochloride salt of the compound of claim 16.

18. A compound of claim 3 which is α-amino-4-hydroxy-1,3-benzenediacetic acid.

19. A pharmaceutical composition for treating stroke which comprises an effective amount of the compound of claim 1 and a pharmacologically acceptable carrier.

20. A pharmaceutical composition for treating stroke which comprises an effective amount of the compound of claim 11 and a pharmacologically acceptable carrier.

21. A pharmaceutical composition for treating stroke in a human suffering therefrom which comprises administering a compound of the claim 1 in unit dosage form.

22. A pharmaceutical composition for treating stroke in a human suffering therefrom which comprises administering a compound of the claim 11 in unit dosage form.

* * * * *